(12) United States Patent
Abe

(10) Patent No.: US 8,275,174 B2
(45) Date of Patent: Sep. 25, 2012

(54) VEIN PATTERN MANAGEMENT SYSTEM, VEIN PATTERN REGISTRATION APPARATUS, VEIN PATTERN AUTHENTICATION APPARATUS, VEIN PATTERN REGISTRATION METHOD, VEIN PATTERN AUTHENTICATION METHOD, PROGRAM, AND VEIN DATA CONFIGURATION

(75) Inventor: Hiroshi Abe, Tokyo (JP)

(73) Assignee: Sony Corporation, Tokyo (JP)

( * ) Notice: Subject to any disclaimer, the term of this patent is extended or adjusted under 35 U.S.C. 154(b) by 284 days.

(21) Appl. No.: 12/600,069

(22) PCT Filed: May 13, 2008

(86) PCT No.: PCT/JP2008/058761
§ 371 (c)(1),
(2), (4) Date: Nov. 13, 2009

(87) PCT Pub. No.: WO2008/140077
PCT Pub. Date: Nov. 20, 2008

(65) Prior Publication Data
US 2010/0215223 A1 Aug. 26, 2010

(30) Foreign Application Priority Data
May 16, 2007 (JP) ................................. 2007-130858

(51) Int. Cl.
*G06K 9/00* (2006.01)
(52) U.S. Cl. ....................................... 382/115; 382/124
(58) Field of Classification Search ........................ None
See application file for complete search history.

(56) References Cited

U.S. PATENT DOCUMENTS 7,054,811 B2 * 5/2006 Barzilay ........................ 704/246
7,526,111 B2 * 4/2009 Miura et al. .................. 382/126
7,806,852 B1 * 10/2010 Jurson ............................ 604/65
(Continued)

FOREIGN PATENT DOCUMENTS

JP    2001-184483    7/2001
(Continued)

OTHER PUBLICATIONS

T. Matsumoto, "Biometric Authentication in Financial Transactions", 9th Study Group on Problem of Forged ATM Cards, Financial Services Agency, pp. 1-32 (2005).

(Continued)

*Primary Examiner* — Wesley Tucker
*Assistant Examiner* — Nancy Bitar
(74) *Attorney, Agent, or Firm* — Finnegan, Henderson, Farabow, Garrett & Dunner, L.L.P.

(57) ABSTRACT

An imaging unit capturing an image of a body surface with near-infrared light while changing a magnification, and generating multiple pieces of near-infrared light imaging data having different magnifications, a vein pattern extraction unit extracting multiple vein patterns corresponding to each of the multiple pieces of the near-infrared light imaging data from each of the multiple pieces of the near-infrared light imaging data, a fractal dimension calculation unit calculating a fractal dimension corresponding to each of the vein patterns for the extracted multiple vein patterns, and a pseudo-vein pattern determination unit determining presence of a pseudo-vein pattern intentionally formed on a part of the captured body surface based on the calculated fractal dimension are provided.

6 Claims, 9 Drawing Sheets

U.S. PATENT DOCUMENTS

| | | | | |
|---|---|---|---|---|
| 2002/0186875 | A1* | 12/2002 | Burmer et al. | 382/133 |
| 2005/0180620 | A1* | 8/2005 | Takiguchi | 382/128 |
| 2007/0055123 | A1* | 3/2007 | Takiguchi | 600/407 |
| 2007/0116330 | A1* | 5/2007 | Takiguchi | 382/115 |
| 2007/0244409 | A1* | 10/2007 | Takiguchi | 600/547 |
| 2009/0129635 | A1* | 5/2009 | Abe | 382/115 |

FOREIGN PATENT DOCUMENTS

| | | |
|---|---|---|
| JP | 2003-93368 | 4/2003 |
| JP | 2005-56282 | 3/2005 |
| JP | 2005-71118 | 3/2005 |
| JP | 2005-259345 | 9/2005 |
| JP | 2007-050158 | 3/2007 |
| JP | 2007-50158 | 3/2007 |

OTHER PUBLICATIONS

EPO Communication dated Mar. 6, 2012, including a Supplementary European Search Report for EP Application No. 08752641.4 (3 pages).

EPO Communication dated May 8, 2012, including Form 2906, for EP Application No. 08752641.4 (6 pages).

* cited by examiner

VEIN PATTERN MANAGEMENT SYSTEM, VEIN PATTERN REGISTRATION APPARATUS, VEIN PATTERN AUTHENTICATION APPARATUS, VEIN PATTERN REGISTRATION METHOD, VEIN PATTERN AUTHENTICATION METHOD, PROGRAM, AND VEIN DATA CONFIGURATION

CROSS REFERENCE TO RELATED APPLICATIONS

This application is a national phase application based on PCT/JP2008/058761, filed May 13, 2008, which claims the priority of Japanese Patent Application No. 2007-130858, filed May 16, 2007, the contents of all of which are incorporated herein by reference.

TECHNICAL FIELD

The present invention relates to a vein pattern management system, a vein pattern registration apparatus, a vein pattern authentication apparatus, a vein pattern registration method, a vein pattern authentication method, a program, and a vein data configuration.

BACKGROUND ART

Individual authentication methods include a method for authenticating an individual by registering a fingerprint, a voiceprint, an iris, and a retina of the individual, or a vein pattern of the back of the individual's hand or the individual's finger, or the like as registered data in advance, and verifying and determining data input at the time of authentication and the registered data. In particular, individual authentication using the vein pattern has recently been focused on due to its high discriminating ability.

For the purpose of improving security of the above-mentioned individual authentication methods, since it is essential to block illegal users attempting to impersonate normal authenticated users, methods for blocking such illegal users have been widely developed (for example, refer to Patent Document 1 and Non-Patent Document 1).

PRIOR ART DOCUMENT

[Patent Document 1] Japanese Patent Application Publication No. 2005-259345
[Non-Patent Document 1] Tsutomu Matsumoto, "Biometric Authentication in Financial Transactions", the 9th Study Group on Problem of Forged ATM Cards", Financial Services Agency, Apr. 15, 2005

In some individual authentication methods using a vein pattern, the vein pattern is extracted by capturing an image of a backside or a finger of a hand with near-infrared light and processing extracted imaging data using a differential filter.

However, since the differential filter used to the imaging data captured with the near-infrared light into a vein portion and a non-vein portion is apt to output a pseudo-vein pattern, which has been drawn on a body surface with a felt-tip pen and the like, as a vein portion, there is a need for a method for determining presence of such a pseudo-vein pattern in order to avoid impersonation by an illegal user.

The present invention has been made in consideration of the above-mentioned problems, and an object of the present invention is to provide a novel and improved vein pattern management system, vein pattern registration apparatus, vein pattern authentication apparatus, vein pattern registration method, vein pattern authentication method, program, and vein data configuration, capable of determining presence of a pseudo-vein pattern intentionally produced on a body surface.

DISCLOSURE OF THE INVENTION

In order to solve the above problem, according to an embodiment of the invention, there is provided a vein pattern management system for registering and authenticating a vein pattern acquired by radiating light to a portion of a living body, including: an imaging unit for capturing an image of a body surface of the portion of the living body with near-infrared light while changing a magnification, and generating multiple pieces of near-infrared light imaging data having different magnifications; a vein pattern extraction unit for extracting multiple vein patterns corresponding to each of the multiple pieces of the near-infrared light imaging data from each of the multiple pieces of the near-infrared light imaging data; a fractal dimension calculation unit for calculating a fractal dimension corresponding to each of the vein patterns for the extracted multiple vein patterns; a pseudo-vein pattern determination unit for determining presence of a pseudo-vein pattern intentionally formed on a part of the captured body surface based on the calculated fractal dimension; a vein pattern registration unit for registering the near-infrared light vein pattern based on a determination result from the determination unit to generate a registered vein pattern; and a vein pattern authentication unit for comparing a newly generated near-infrared light vein pattern with the registered vein pattern based on the determination result from the pseudo-vein pattern determination unit and authenticating the newly generated near-infrared vein pattern.

In order to solve the above problem, according to another embodiment of the invention, there is provided a vein pattern registration apparatus including: an imaging unit for capturing an image of a body surface of a portion of a living body with near-infrared light while changing a magnification, and generating multiple pieces of near-infrared light imaging data having different magnifications; a vein pattern extraction unit for extracting multiple vein patterns corresponding to each of the multiple pieces of the near-infrared light imaging data from each of the multiple pieces of the near-infrared light imaging data; a fractal dimension calculation unit for calculating a fractal dimension corresponding to each of the vein patterns for the extracted multiple vein patterns; a pseudo-vein pattern determination unit for determining presence of a pseudo-vein pattern intentionally formed on a part of the captured body surface based on the calculated fractal dimension; and a vein pattern registration unit for registering the near-infrared light vein pattern based on a determination result from the pseudo-vein pattern determination unit to generate a registered vein pattern.

In order to solve the above problem, according to another embodiment of the invention, there is provided a vein pattern authentication apparatus including: an imaging unit for capturing an image of a body surface of a portion of a living body with near-infrared light while changing a magnification, and generating multiple pieces of near-infrared light imaging data having different magnifications; a vein pattern extraction unit for extracting multiple vein patterns corresponding to each of the multiple pieces of the near-infrared light imaging data from each of the multiple pieces of the near-infrared light imaging data; a fractal dimension calculation unit for calculating a fractal dimension corresponding to each of the vein patterns for the extracted multiple vein patterns; a pseudo-vein pattern determination unit for determining presence of a pseudo-vein pattern intentionally formed on a part of the captured body surface based on the calculated fractal dimension; and a vein pattern authentication unit for comparing an already registered vein pattern with the near-infrared light vein pattern and authenticating the near-infrared light vein pattern based on a determination result from the pseudo-vein pattern determination unit.

The pseudo-vein pattern determination unit may determine that the pseudo-vein pattern is present when the calculated fractal dimension is less than a predetermined threshold value of a fractal dimension, and determine that the pseudo-vein pattern is not present when the calculated fractal dimension is greater than the predetermined threshold value of the fractal dimension.

The fractal dimension calculation unit may calculate the fractal dimension using a box-counting method for a plurality of pixels constituting the vein pattern.

Further, the vein pattern extraction unit may extract the near-infrared light vein pattern using a differential filter that outputs a large value for a pixel having a large difference between the pixel and its surrounding pixel for a plurality of pixels constituting the near-infrared light imaging data.

The differential filter may be a derivative filter or a Laplacian of Gaussian (Log) filter.

In addition, the vein pattern authentication unit may authenticate the near-infrared light vein pattern based on the registered vein pattern acquired from the vein pattern registration apparatus, or may authenticate the near-infrared light vein pattern based on the registered vein pattern registered within the vein pattern authentication apparatus.

In order to solve the above problem, according to another embodiment of the invention, there is provided a vein pattern registration method for registering a vein pattern acquired by radiating light to a portion of a living body, including the steps of: capturing an image of a body surface of the portion of the living body with near-infrared light while changing a magnification, and generating multiple pieces of near-infrared light imaging data having different magnifications; extracting multiple vein patterns corresponding to each of the multiple pieces of the near-infrared light imaging data from each of the multiple pieces of the near-infrared light imaging data; calculating a fractal dimension corresponding to each of the vein patterns for the extracted multiple vein patterns; determining presence of a pseudo-vein pattern intentionally formed on a part of the captured body surface based on the calculated fractal dimension; and registering the vein pattern as a registered vein pattern based on a determination result.

In order to solve the above problem, according to another embodiment of the invention, there is provided a vein pattern authentication method for authenticating a vein pattern acquired by radiating light to a portion of a living body, including the steps of: capturing an image of a body surface of the portion of the living body with near-infrared light while changing a magnification, and generating multiple pieces of near-infrared light imaging data having different magnifications; extracting multiple vein patterns corresponding to each of the multiple pieces of the near-infrared light imaging data from each of the multiple pieces of the near-infrared light imaging data; calculating a fractal dimension corresponding to each of the vein patterns for the extracted multiple vein patterns; determining presence of a pseudo-vein pattern intentionally formed on a part of the captured body surface based on the calculated fractal dimension; and comparing the vein pattern with an already registered near-infrared light vein pattern based on a determination result and authenticating the vein pattern.

In the step of determining presence of a pseudo-vein pattern, it may be determined that the pseudo-vein pattern is present when the calculated fractal dimension is less than a predetermined threshold value of a fractal dimension; and it may be determined that the pseudo-vein pattern is not present when the calculated fractal dimension is greater than the predetermined threshold value of the fractal dimension.

In the step of calculating a fractal dimension, a box-counting method may be used for a plurality of pixels constituting the vein pattern.

In the step of extracting multiple vein patterns, a differential filter that outputs a high value for a pixel having a large difference between the pixel and its surrounding pixel may be used for a plurality of pixels constituting the near-infrared light imaging data.

The differential filter may be a derivative filter or a Laplacian of Gaussian (Log) filter.

In order to solve the above problem, according to another embodiment of the invention, there is provided a program for causing a computer controlling a vein pattern registration apparatus for registering a vein pattern acquired by radiating light to a portion of a living body to execute: an imaging function for capturing an image of a body surface of the portion of the living body with near-infrared light while changing a magnification, and generating multiple pieces of near-infrared light imaging data having different magnifications; a vein pattern extraction function for extracting multiple vein patterns corresponding to each of the multiple pieces of the near-infrared light imaging data from each of the multiple pieces of the near-infrared light imaging data; a fractal dimension calculation function for calculating a fractal dimension corresponding to each of the vein patterns for the extracted multiple vein patterns; a pseudo-vein pattern determination function for determining presence of a pseudo-vein pattern intentionally formed on a part of the captured body surface based on the calculated fractal dimension; and a vein pattern registration function for registering the near-infrared light vein pattern based on a determination result from the pseudo-vein pattern determination unit to generate a registered vein pattern.

According to this configuration, a computer program is stored in a storage unit included in a computer, and read and executed by CPU included in the computer so that the computer program causes the computer to operate as the above-mentioned vein pattern registration apparatus. In addition, there can be also provided a computer readable recording medium in which the computer program is recorded. The recording medium may be, for example, a magnetic disk, an optical disk, a magnetic optical disk, a flush memory, and the like. Furthermore, the above-mentioned computer program may be distributed via a network without using a recording medium.

In order to solve the above problem, according to another embodiment of the invention, there is provided a program for causing a computer controlling a vein pattern authentication apparatus for authenticating a vein pattern acquired by radiating light to a portion of a living body to execute: an imaging function for capturing an image of a body surface of the portion of the living body with near-infrared light while changing a magnification, and generating multiple pieces of near-infrared light imaging data having different magnifications; a vein pattern extraction function for extracting multiple vein patterns corresponding to each of the multiple pieces of the near-infrared light imaging data from each of the multiple pieces of the near-infrared light imaging data; a fractal dimension calculation function for calculating a fractal dimension corresponding to each of the vein patterns for the extracted multiple vein patterns; a pseudo-vein pattern determination function for determining presence of a pseudo-vein pattern intentionally formed on a part of the captured body surface based on the calculated fractal dimension; and a vein pattern authentication function for comparing an already registered vein pattern with the near-infrared light vein pattern and authenticating the near-infrared light vein pattern based on a determination result from the pseudo-vein pattern determination unit.

According to this configuration, a computer program is stored in a storage unit included in a computer, and read and executed by CPU included in the computer so that the computer program causes the computer to operate as the above-mentioned vein pattern authentication apparatus. In addition, there can be also provided a computer readable recording medium in which the computer program is recorded. The recording medium may be, for example, a magnetic disk, an optical disk, a magnetic optical disk, a flush memory, and the like. Furthermore, the above-mentioned computer program may be distributed via a network without using a recording medium.

In order to solve the above problem, according to another embodiment of the invention, there is provided a vein data configuration including: a vein data storage area containing data that correspond to a vein pattern of an individual and are to be verified with image data that is subject to be verified and is acquired by capturing an image with near-infrared light; and a fractal dimension storage area containing a fractal dimension of the vein pattern of the individual.

The vein data configuration may further include a parameter storage area containing a parameter changing an output property of a differential filter outputting a high output for an pixel that differs largely from its surrounding pixels, for each pixel constituting the image data acquired by capturing the image with the near-infrared light, and the parameter significantly may change an output value of the differential filter, when the image data acquired by capturing the image with the near-infrared light have a difference greater than that between a value indicating a vein portion and a value indicating a non-vein portion.

According to embodiments of the present invention, presence of a pseudo-vein pattern intentionally produced on a body surface can be determined.

EXPLANATION OF NUMERAL

Figure 1:
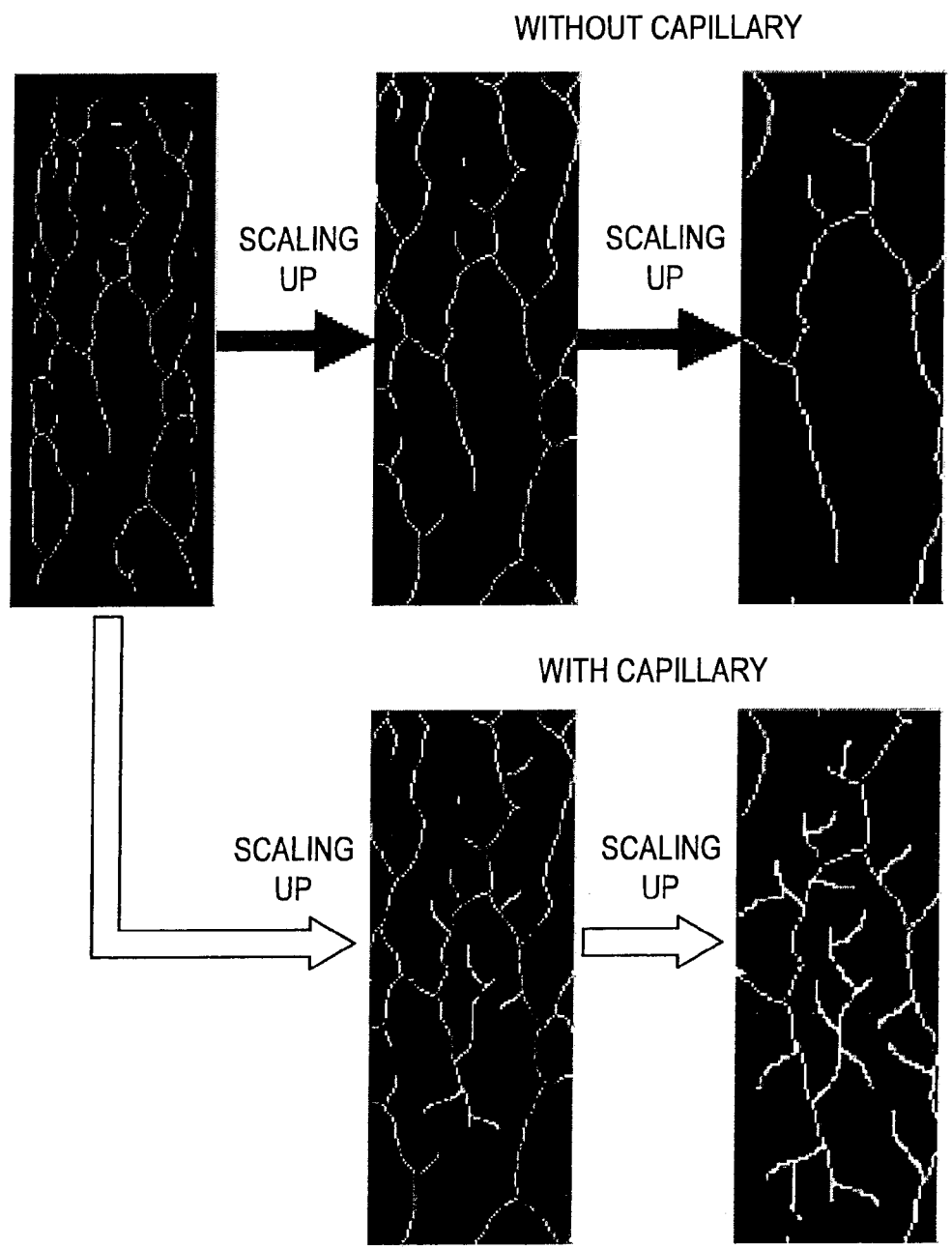
FIG. 1 is an explanatory diagram illustrating self-similarity of a vein pattern.

| 10 | vein pattern management system |
|---|---|
| 12 | network |
| 14 | removable recording medium |
| 20 | vein pattern registration apparatus |
| 30 | vein pattern authentication apparatus |
| 201 | CPU |
| 203 | ROM |
| 205 | RAM |
| 207 | bus |
| 211 | imaging device |
| 213 | input device |
| 215 | output device |
| 217 | storage device |
| 219 | drive |
| 221 | communication device |
| 231, 301 | imaging unit |
| 233, 303 | radiation unit |
| 235, 305 | near-infrared light |
| 237, 307 | optical lens |
| 239, 309 | imaging data generation unit |
| 241, 311 | vein pattern extraction unit |
| 251, 321 | fractal dimension calculation unit |
| 261, 331 | pseudo-vein pattern determination unit |
| 271, 341 | vein pattern registration unit |
| 273, 343 | storage unit |
| 275 | registered vein pattern disclosure unit |
| H | body surface |

BEST MODE FOR CARRYING OUT THE INVENTION (First Embodiment)

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

Although, in a later description, the present invention will be described in connection with an example of vein patterns of fingers, the present invention is not limited to this example.
<Pseudo-Vein Pattern>

A pseudo-vein pattern intentionally formed on a finger surface will be described as an example of pseudo-vein patterns in preparation for a description of a vein pattern management system according to a first embodiment of the present invention.

In biometric authentication with finger vein pattern, although impersonation is difficult because a vein pattern itself is located inside of a finger, it is also difficult, in extraction of the vein pattern, to determine whether an extracted vein pattern is located inside of the finger. Since a vein per se absorbs near-infrared light, the vein is imaged as a dark shadow while capturing an image of a body surface, and if a pseudo-vein pattern is drawn on the body surface with a component, which has absorbency similar to that of the vein, the pseudo-vein pattern might be indistinguishable from the vein pattern.

Since the near-infrared light is permeable to body tissue, on one hand, and is absorbable in hemoglobin in blood (reduced hemoglobin), on the other hand, veins distributed inside of a finger, a palm of a hand, or a back of a hand appear as shadows in an image when the near-infrared light is radiated to the finger, the palm of the hand, or the back of the hand. The shadows of the vein appearing on the image are referred to as a vein pattern.

Figure 9:
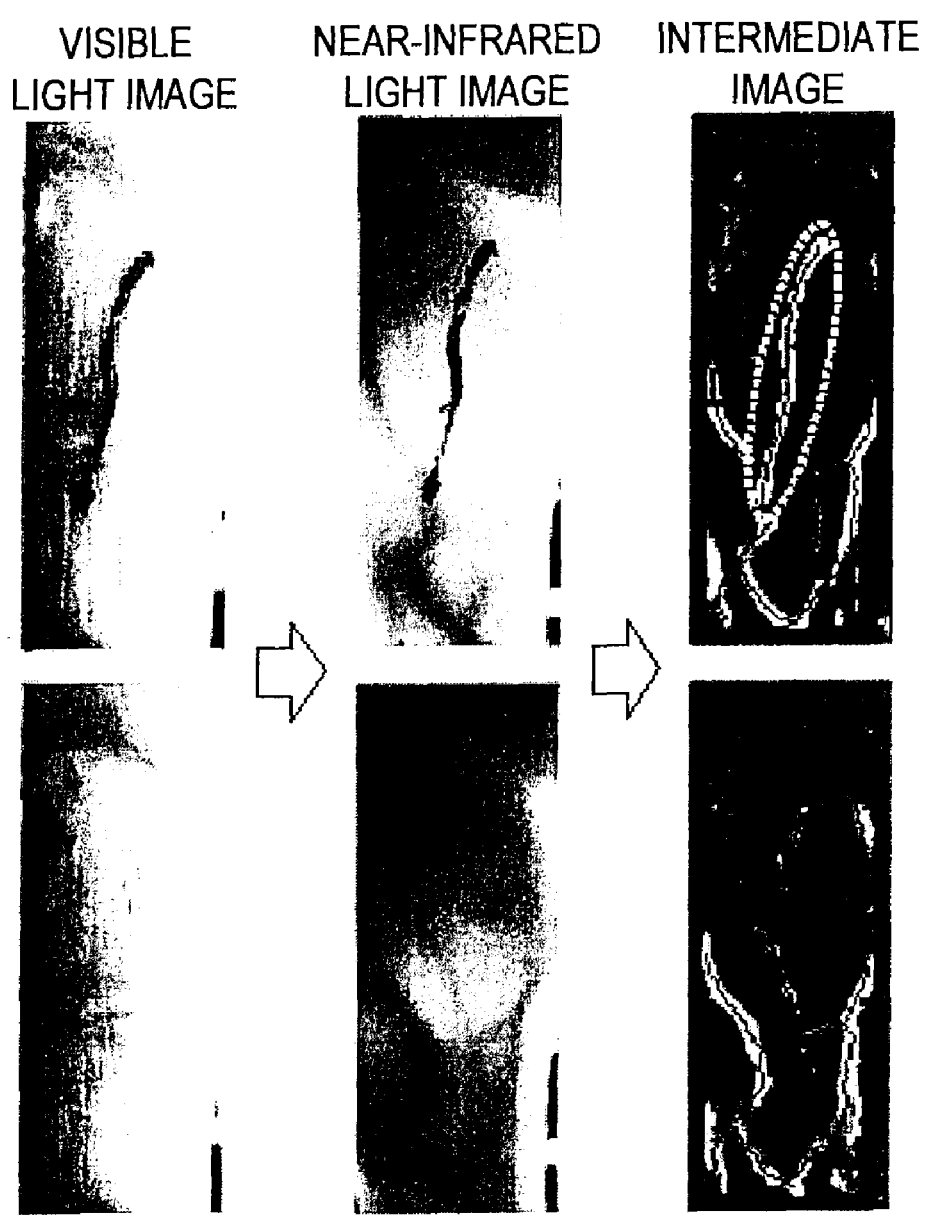
FIG. 9 is an explanatory diagram illustrating a pseudo-vein pattern drawn on a finger surface.

FIG. 9 is an explanatory diagram illustrating a pseudo-vein pattern drawn on a finger surface. The upper part of FIG. 9 represents a case in which a pseudo-vein pattern is directly drawn on a finger surface with a permanent pen, and the lower part of FIG. 9 represents a case in which no pseudo-vein patterns are drawn on the finger surface. In addition, in either of the upper and lower parts, there are shown from left to right a captured image with visible light, a captured image with near-infrared light, and an image subject to a threshold process of an output of a Laplacian of Gaussian (Log) filter that is a kind of differential filters, respectively.

The threshold process as used herein refers to a process in which predetermined upper and lower threshold values are assigned to an output value of a Log filter and the output value is set to zero if the output value is less than the lower threshold value and the output value is set to the upper threshold value if the output value is greater than the upper threshold value.

Since an ink component of the permanent pen has a light absorption property similar to that of reduced hemoglobin in a vein, the pseudo-vein pattern drawn with the permanent pen is left in an intermediate image not yet subject to a thinning process as a vein pattern, as shown in top right and bottom right ends of FIG. 9, and is ultimately recognized as a vein in the finger.

In order to solve such problems, the inventors of this application has been dedicated to developing so that the inventor has contrived a vein pattern management system, an vein pattern registration apparatus, a vein pattern authentication apparatus, a vein pattern registration method, a vein pattern authentication method, a program, and a vein data configuration.

<Present Embodiment>
(Self-Similarity of Capillary)

Figure 2:
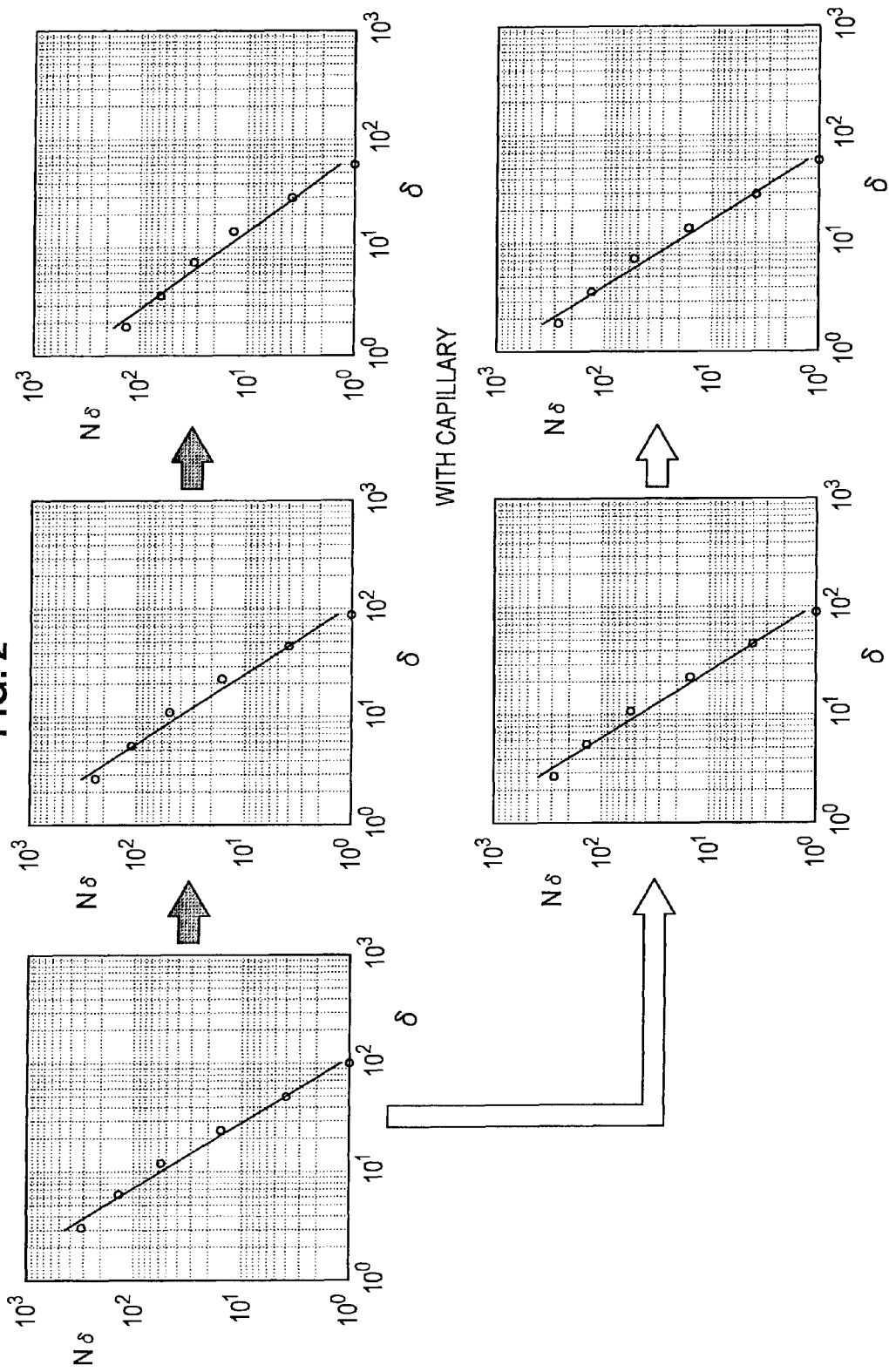
FIG. 2 is an explanatory diagram illustrating a plotting chart to calculate a fractal dimension.
Figure 3:
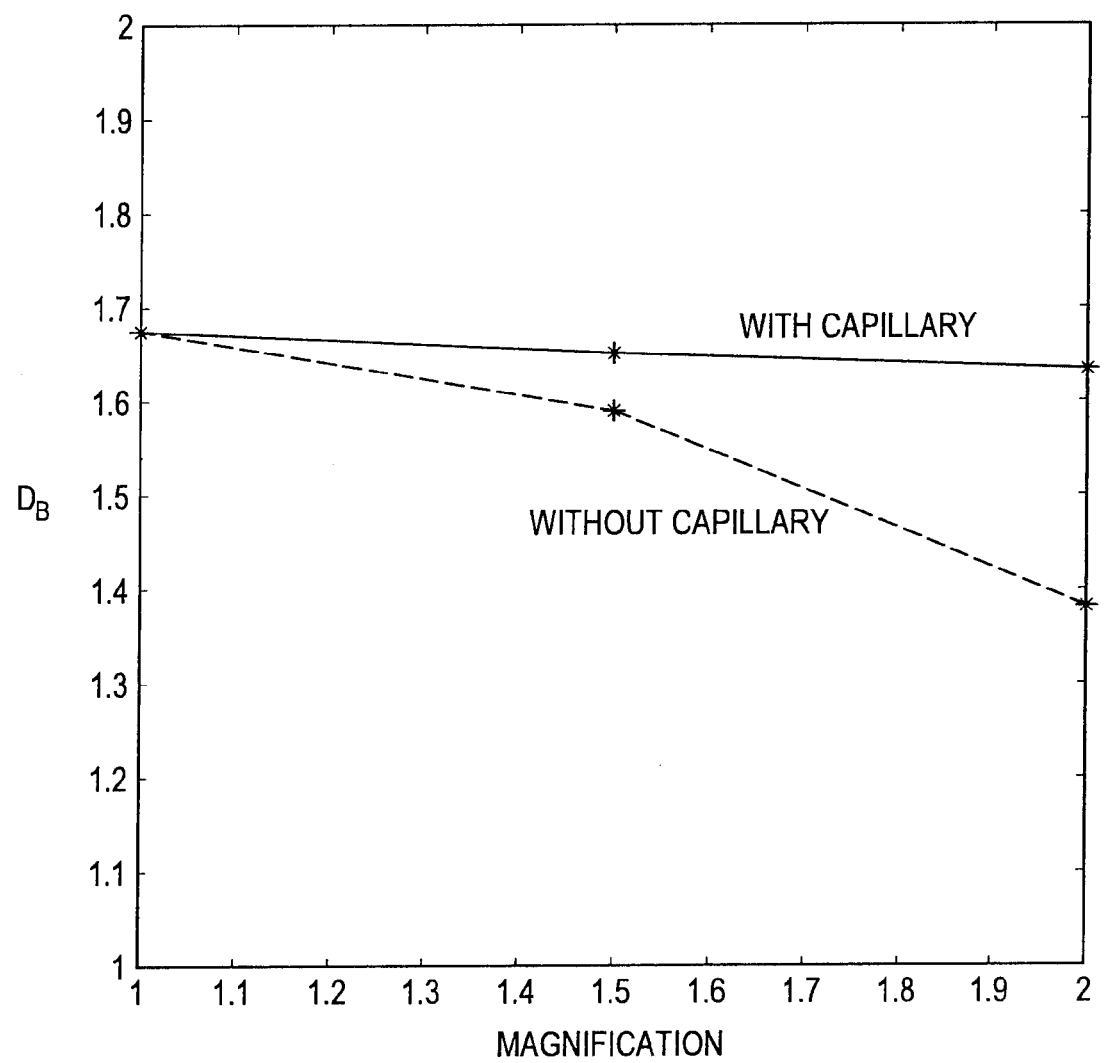
FIG. 3 is a graph illustrating a change in a fractal dimension.

Referring to FIG. 1 to FIG. 3, a self-similarity of a capillary will be described in detail. FIG. 1 is a diagram illustrating a self-similarity of a vein pattern, FIG. 2 is an explanatory diagram illustrating a plotting chart to calculate a fractal dimension, and FIG. 3 is a graph illustrating a change in a fractal dimension.

It is known that a human blood vessel (especially capillary) has a self-similarity (fractal nature). For example, on one hand, when capturing an image of a finger surface while changing a magnification, a capillary that otherwise would not be found by a conventional magnification begins to emerge with being scaled up. On the other hand, when attempting to form a vein pattern in a pseudo-manner on an artificially produced finger or the like, it is very difficult to create a capillary that newly emerges by capturing an image with scaling up.

In other words, as shown in FIG. 1, although in case of a living body (that is to say, in presence of a capillary), a visible vein pattern would not significantly diminish due to its self-similarity in spite of increasing a magnification, in case of a non-living body (that is to say, in absence of a capillary where a pseudo-vein pattern is formed), a newly emerging vein pattern is supposed to significantly diminish as the magnification is increased in capturing.

Based on the above-mentioned knowledge, the inventor of this application has been dedicated to developing so that the inventor has found that it is possible to distinguish between presence and absence of a pseudo-vein pattern, that is to say, distinguish between a living body and a non-living body by a change in a fractal dimension acquired by capturing images of a body surface with multiple magnifications, respectively, and calculating the fractal dimension of a vein pattern derived from captured images.

FIG. 2 shows, for each of vein patterns shown in FIG. 1 (in case of a magnification of 1, 1.5, and 2 in series, from left to right, in FIG. 1), a result of calculation of a fractal dimension using a box-counting method that is a kind of fractal dimension calculation methods. The box-counting method to be described later involves counting a number of required boxes in case that it is intended to cover all of the vein patterns with boxes having a size of a. In the box-counting method, a gradient (inclination) of a line corresponds to a fractal dimension when plotting a log-log graph by taking the size, $\sigma$, of the box as an abscissa axis and the number of the required boxes as an ordinate axis.

FIG. 3 is a graph illustrating a change in a fractal dimension when a magnification is taken along an abscissa axis and a fractal dimension derived from FIG. 2 is taken along an ordinate axis. Referring to FIG. 3, it can be seen that, in presence of capillary (i.e., in case of a living body without a pseudo-vein pattern), a fractal dimension maintains a constant value, whereas in absence of a capillary (i.e., in case of a non-living body with a pseudo-vein pattern), a fractal dimension significantly reduces as a magnification increases.

This may probably be because, in a pseudo-vein pattern where no capillaries emerge, a vein pattern significantly diminishes and a fractal dimension reduces due to scaling up, whereas, in case of a living body, although a capitally newly emerges and a vein pattern per se changes due to the scaling up, complexity of the pattern changes a little and a fractal dimension maintains a stable value.

As described above, it is appreciated that presence of a pseudo-vein pattern can be distinguished by setting a predetermined threshold value for a fractal dimension in advance, and comparing the predetermined threshold value with a fractal dimension of a near-infrared light vein pattern acquired by capturing an image.

(Vein Pattern Management System)

Figure 4:
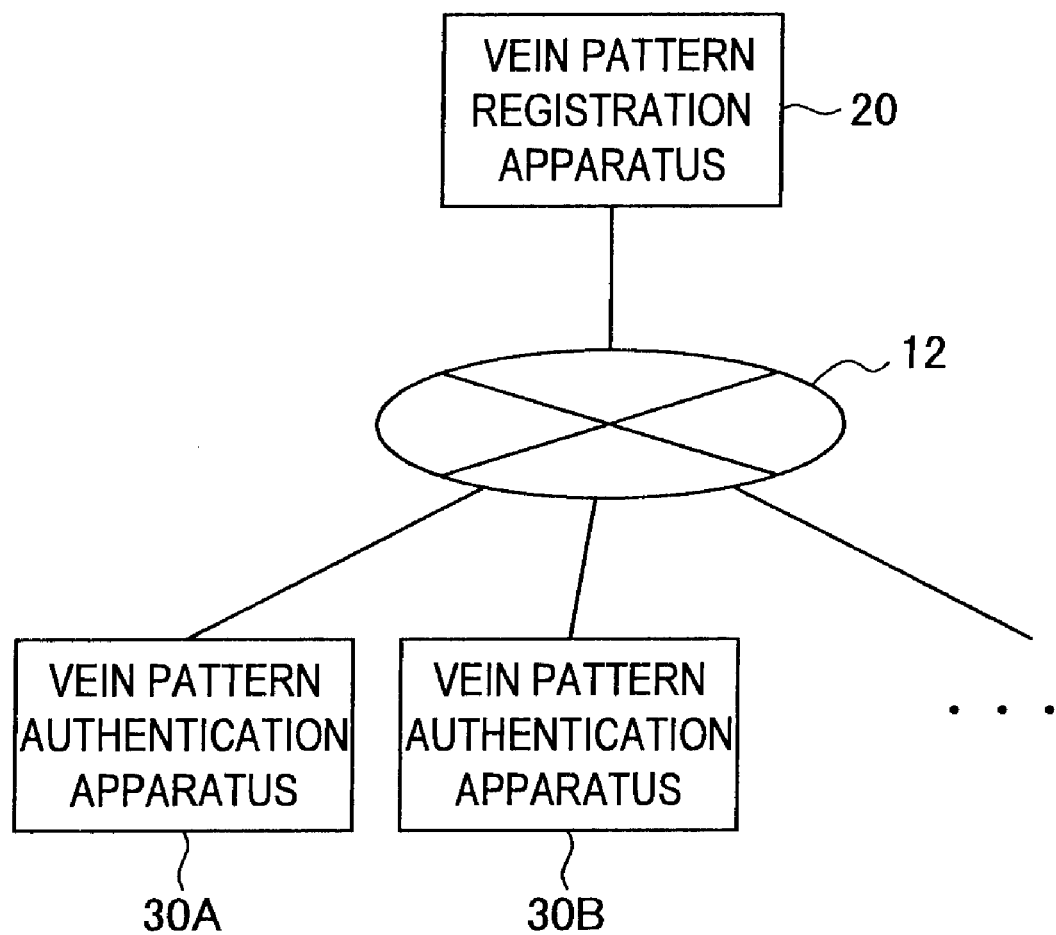
FIG. 4 is an explanatory diagram illustrating a vein pattern management system according to an embodiment of the present invention.

Next, referring to FIG. 4, a vein pattern management system 10 according to this embodiment will be described in detail. FIG. 4 is an explanatory diagram illustrating the vein pattern management system 10 according to this embodiment.

As shown in FIG. 4, the vein pattern management system 10 include, for example, a vein pattern registration apparatus 20, and a plurality of vein pattern authentication apparatuses 30A, 30B, . . . , which are connected to the vein pattern registration apparatus 20 via a network 12.

The network 12 is a communication line network that connects the vein pattern registration apparatus 20 and a vein pattern authentication apparatus 30 such that they can communicate in either unidirection or bidirection. The network 12 may include, for example, public network, such as Internet, telephone network, satellite communication network, or multicasting network, private network, such as Wide Area Network (WAN), Local Area Network (LAN), Internet Protocol-Virtual Private Network (IP-VPN), Ethernet (registered trademark), or wireless LAN, and the like, and is limited neither to wired network nor wireless network.

The vein pattern registration apparatus 20 is operable to radiate light of a predetermined wavelength to a body surface of an individual desiring to register his/her vein pattern, capture an image of the body surface, extract a vein pattern from the captured image data, and register the extracted vein pattern as personal identity information. The vein pattern registration apparatus 20 is also operable to determine presence of a pseudo-vein pattern intentionally formed on the body surface and determine whether the extracted vein pattern should be registered or not. In addition, the vein pattern registration apparatus 20 may disclose registered vein patterns, which have been registered as the personal identity information, as required by the vein pattern authentication apparatus 30 to be described later.

The vein pattern authentication apparatuses 30A and 30B are operable to radiate light of the predetermined wavelength to a body surface of an individual desiring to register his/her vein pattern, capture an image of the body surface, extract a vein pattern from the captured image data, and compare the extracted vein pattern with already registered vein patterns to authenticate the individual. The vein pattern authentication apparatus 30 is also operable to determine presence of a pseudo-vein pattern intentionally formed on the body surface and determine whether the extracted vein pattern should be authenticated or not. In addition, the vein pattern authentication apparatuses 30A and 30B may request the vein pattern registration apparatus 20 to disclose the already registered vein patterns.

It is noted that the vein pattern registration apparatus 20 and the vein pattern authentication apparatus 30A and 30B may be connected via the network 12 as shown in the figures, or may be directly connected via a Universal Serial Bus (USB) port, an IEEE 1394 port, such as an i.LINK, a Small Computer System Interface (SCSI) port, a RS-232C port, or the like, not via the network 12.

Although, in FIG. 4, there is only one vein pattern registration apparatus 20 connected to a network 12, this embodiment is not intended to be limited to a configuration as described above, but may allow a plurality of vein pattern registration apparatuses 20 to be connected on the network 12. Similarly, in FIG. 4, there are only two vein pattern authentication apparatuses 30 which are connected to the network 12, and a plurality of vein pattern authentication apparatuses 30 may be connected on the network 12.

(Configuration of Vein Pattern Registration Apparatus 20)

Figure 5:
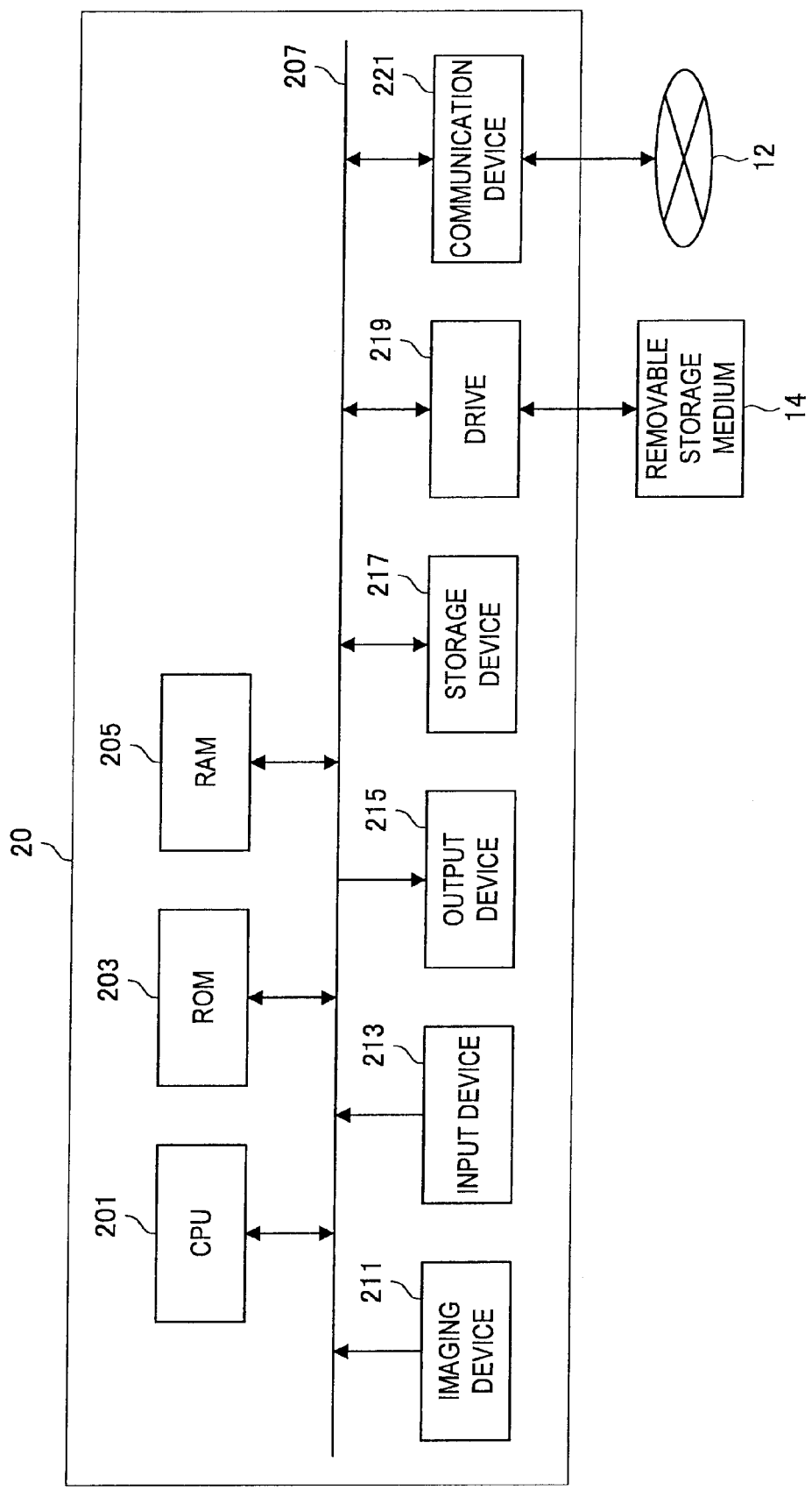
FIG. 5 is a block diagram illustrating a hardware configuration of a vein pattern registration apparatus according to the embodiment.

Referring to FIG. 5, a hardware configuration of a vein pattern registration apparatus 20 according to this embodiment will be described in detail. FIG. 5 is a block diagram illustrating the hardware configuration of the vein pattern registration apparatus 20 according to this embodiment.

As shown in FIG. 5, the vein pattern registration apparatus 20 mainly includes Central Processing Unit (CPU) 201, Read Only Memory (ROM) 203, Random Access Memory (RAM) 205, a bus 207, an imaging device 211, an input device 213, an output device 215, a storage device 217, a drive 219, and a communication device 221.

CPU 201 serves as a computing device and a controller for controlling all or a part of operations in the vein pattern registration apparatus 20 in accordance with various programs recorded in ROM 203, RAM 205, the storage device 217 or a removable recording medium 14. ROM 203 stores programs, operational parameters, and the like used by CPU 201. RAM 205 temporarily stores a program for use in execution by CPU 201, parameters that change appropriately in the execution of the program, and the like. CPU, ROM, and RAM are connected with each other via the bus 207 formed by an internal bus, such as a CPU bus.

The imaging device 211 is a device that captures an image of a body surface to generate image data under control of CPU 201. The imaging device 211 includes, for example, a radiation device for radiating light of a predetermined wavelength and a focusing device, such as an optical lens, for focusing light transmitting through the body surface. The radiation device includes a light source emitting the light of the predetermined wavelength and radiates the light of the predetermined wavelength based on a control signal from CPU 201. The focusing device collects the light radiated from the radiation device and generates the image data.

The input device 213 includes, for example, an operation means, such as mouse, a keyboard, a touch panel, a button, a switch, and a lever, which is operated by a user, and an audio input means, such as a microphone and a headset. In addition, the input device 213 may be, for example, a remote control means (what is called remote controller) using infrared radiation or other radio waves, or may be an external connection device, such as a mobile telephone and PDA, adapted to the operation of the vein pattern registration apparatus 20. Furthermore, the input device 213 may include, for example, an input control circuit or the like, for generating an input signal based on information input by the user using the above-mentioned operation means and audio input means and outputting the input signal to CPU 201. The user of the vein pattern registration apparatus 20 can input various data and instruct a processing operation to the vein pattern registration apparatus 20 by operating the input device 213.

The output device 215 includes, for example, a display device, such as a Cathode Ray Tube (CRT) display device, a Liquid Crystal Display (LCD) device, a Plasma Display Panel (PDP) device, an Electro-Luminescence (EL) display device and a lamp, an audio output device, such as a speaker and head phones, a printer, a mobile phone, a facsimile machine, and the like, which are capable of visually or audibly communicating acquired information to the user.

The storage device 217 is a data storing device, which is configured as an example of a storage unit of the vein pattern registration apparatus 20 according to this embodiment, and includes, for example, a magnetic storage device, such as a hard disk drive (HDD), a semiconductor storage device, an optical storage device, a magnetic optical storage device, or the like. The storage device 217 stores a wide variety of data, such as programs executed by CPU 201, various data, and various types of data acquired from an outside.

The drive 219 is a reader/writer for a storing medium and may be embedded in or attached externally to the vein pattern registration apparatus 20. The drive 219 reads out information recorded in the removable recording medium 14, such as an attached magnetic disk, optical disk, magnetic optical disk, or semiconductor memory, and outputs the information to RAM 205. In addition, the drive 219 is capable of writing recordings to the removable recording medium 14, such as the attached magnetic disk, optical disk, magnetic optical disk, or semiconductor memory. The removable recording medium 14 includes, for example, a DVD medium, a HD-DVD medium, a Blu-ray medium, CompactFlash (CF) (registered trademark), a memory stick, a Secure Digital (SD) memory card, or the like. In addition, the removable recording medium 14 may be, for example, in a form of an Integrated Circuit (IC) card equipped with a non-contact IC chip, an electronic device, or the like.

The communication device 221 is a communication interface, which include, for example, a communication device for connecting to a communication network 12. The communication device 221 is made in a form of a communication card for use in wired or wireless Local Area Network (LAN), Bluetooth, or Wireless USB (WUSB), a router for use in optical communication, a router for use in Asymmetric Digital Subscriber Line (ADSL), a modem for use in various communication environments, or the like. This communication device 221 is capable of sending/receiving signals and the like to/from other vein pattern registration devices 20 and other vein pattern authentication devices 30. In addition, the network 12 connected to the communication device 221 is formed by networks and the like connected via wired or wireless connection, and may be configured, for example, as Internet, home LAN, infrared communication, satellite communication, or the like.

With a configuration as described above, the vein pattern registration apparatus 20 can radiate light of a predetermined wavelength to a body surface of an individual desiring to register his/her vein pattern, capture an image of the body surface, extract a vein pattern from the captured image data, and register the extracted vein pattern as personal identity information. In addition, the vein pattern registration apparatus 20 can send/receive data to/from the vein pattern authentication apparatus 30 directly connected to the vein pattern registration apparatus 20 or the vein pattern authentication apparatus 30 connected to the network 12, and retrieve information stored in the vein pattern registration apparatus 20 using the removable recording medium 14.

An example of a possible hardware configuration for implementing functions of vein pattern registration apparatus 20 according to this embodiment has been described above. Each of the above components may be configured using a general purpose member, or may be configured with a dedicated hardware for a function of each component. Thus, the hardware configuration used herein can be appropriately modified depending on state of the art at the time of implementing this embodiment.

A description of a hardware configuration of the vein pattern authentication apparatus 30 is omitted, since the hardware configuration of the vein pattern authentication apparatus 30 is substantially identical to that of the vein pattern registration apparatus 20.

Figure 6:
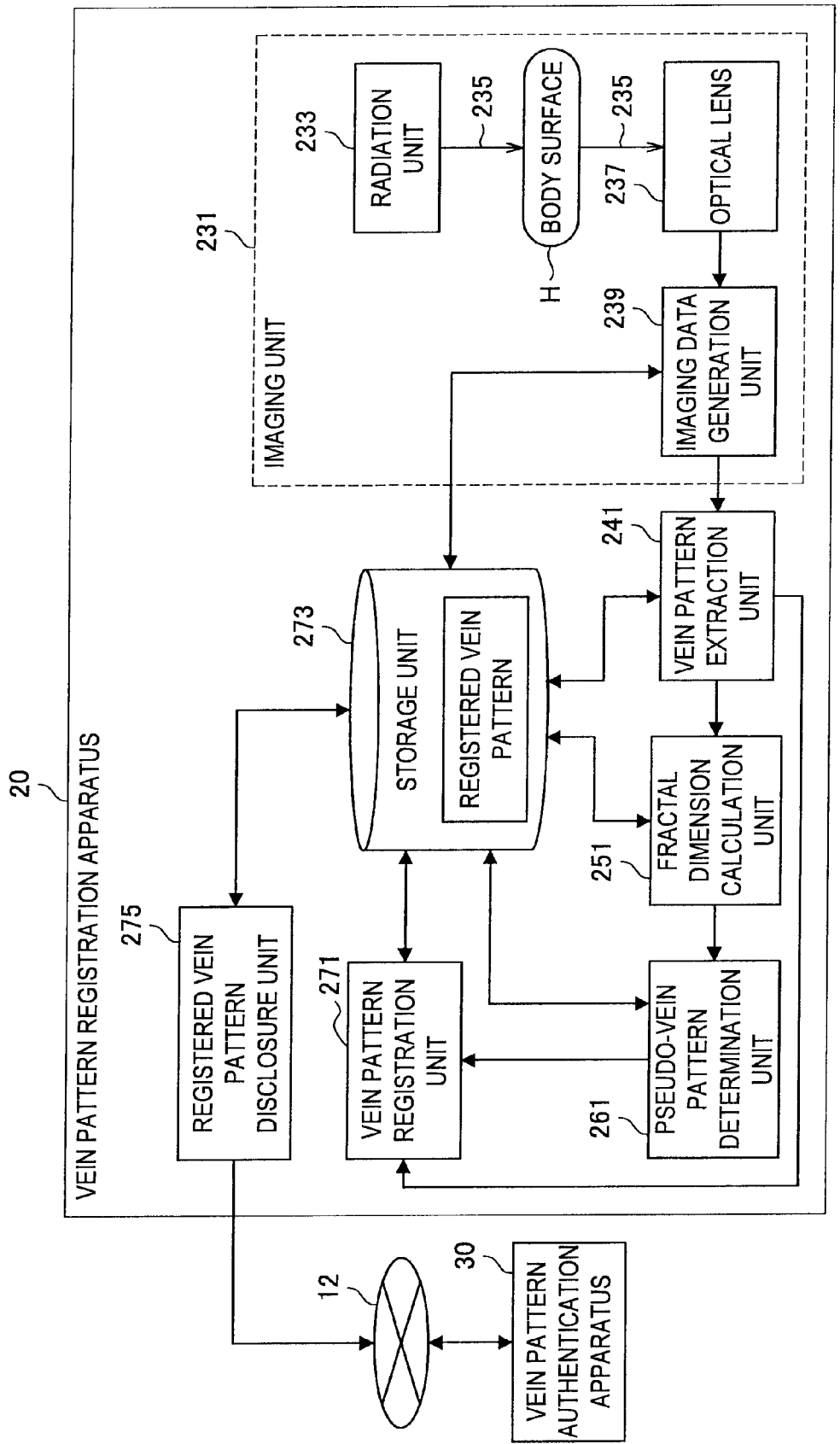
FIG. 6 is a block diagram illustrating a configuration of the vein pattern registration apparatus according to the embodiment.

Next, referring to FIG. 6, a configuration of a vein pattern registration apparatus 20 according to this embodiment will be described in detail. FIG. 6 is a block diagram illustrating the configuration of the vein pattern registration apparatus 20 according to this embodiment.

As shown in FIG. 6, the vein pattern registration apparatus 20 according to this embodiment includes, for example, an imaging unit 231, a vein pattern extraction unit 241, a fractal dimension calculation unit 251, a pseudo-vein pattern determination unit 261, a vein pattern registration unit 271, a storage unit 273, and a registered vein pattern disclosure unit 275.

The imaging unit 231 captures an image of a body surface H of an individual desiring to register his/her vein pattern and generates imaging data. The imaging unit 231 includes, for example, a radiation unit 233 radiating light of a predetermined wavelength, an optical lens 237 focusing light transmitting through the body surface H, and an imaging data generation unit 239 generating imaging data based on the focused light.

The radiation unit 233 includes a light source, such as a halogen lamp and a light emitting diode, which radiates near-infrared light to the body surface H and radiates near-infrared light 235 having a wavelength of about 600 nm to about 1,300 nm.

The optical lens 237 focuses the near-infrared light 235 transmitting through the body surface H, such as a finger surface, and forms an image on the imaging data generation unit 239. The optical lens 237 according to this embodiment is capable of focusing the near-infrared light 235 by changing a magnification to a predetermined magnification. In order to focus the near-infrared light 235 to form an image at various magnifications, the optical lens 237 according to this embodiment may include multiple optical lenses having different focal lengths, respectively, or may include a multifocal lens having a variable focal length.

The imaging data generation unit 239 generates near-infrared light imaging data of various magnifications based on transmitted light of the near-infrared light 235, which has been focused by the optical lens 237. The imaging data generation unit 239 includes, for example, a Charge Coupled Device (CCD) image sensor, a Complementary-Metal Oxide Semiconductor (C-MOS) image sensor, or the like and outputs the near-infrared light imaging data to the vein pattern extraction unit 241 to be described later. In addition, the imaging data generation unit 239 may store the generated near-infrared light imaging data in the storage unit 273 to be described later. In storing in the storage unit 273, date of capture or time of capture may be associated to the generated near-infrared light imaging data. Furthermore, the generated near-infrared light imaging data may be in the form of a Red-Green-Blue (RGB) signal or may be image data of other colors, gray scale image data, or the like.

The vein pattern extraction unit 241 includes, for example, a function of performing a pre-process for vein pattern extraction on the near-infrared light imaging data transmitted from the imaging data generation unit 239, a function of extracting a vein pattern, and a function of performing a post-process for the vein pattern extraction.

The pre-process for the vein pattern extraction includes, for example, a process for detecting a contour of a finger from near-infrared light imaging data and discriminating where the finger is located in the near-infrared light imaging data, a process for rotating the near-infrared light imaging data using the detected contour of the finger and correcting an angle of the near-infrared light imaging data (an angle of captured image), and the like.

In addition, the vein pattern extraction may be achieved by applying a differential filter to the near-infrared light imaging data, which has been subject to detecting the contour or correcting the angle. The differential filter is a filter that outputs a high value as an output value for an image of interest and its surrounding pixels at a portion where differences between the pixel of interest and its surrounding pixels, respectively, are large. In other words, the differential filter as used herein refers to a filter that enhances a line or an edge in an image by an operation using differences in gray level values between a pixel of interest and its surroundings.

In general, performing a filtering process on image data $u(x, y)$ with a variable, which is a lattice point $(x, y)$ on a two-dimensional plane, using a filter $h(x, y)$ results in image data $v(x, y)$, as shown in the following Equation 2. In the following Equation 2, * denotes convolution.

$$v(x, y) = u(x, y) * h(x, y) \qquad (1)$$
$$= \sum_{m_1} \sum_{m_2} h(m_1, m_2) u(x - m_1, y - m_2)$$
$$= \sum_{m_1} \sum_{m_2} u(m_1, m_2) h(x - m_1, y - m_2)$$

In the vein pattern extraction according to this embodiment, a derivative filter, such as a first order spatial derivative filter or a second order spatial derivative filter may be used as the above-mentioned differential filter. The first order spatial derivative filter refers to a filter that, for a pixel of interest, calculates a difference in gray scale levels between the pixel of interest and its horizontally adjacent pixel or its vertically adjacent pixel, and the second order spatial derivative filter refers to a filter that extracts a portion having an increased variation in differences in gray scale values for a pixel of interest.

For example, the following Laplacian of Gaussian (Log) filter can be used as the above-mentioned second order spatial derivative filter. The Log filter (Equation 3) can be written as a second order derivative of a Gaussian filter (Equation 2), which is a smoothing filter using a Gauss function. In the following Equation 2, σ represents a standard deviation of the Gauss function, in other words, a variable representing a degree of smoothing for the Gaussian filter. Furthermore, a in the following Equation 3 is also a parameter, which represent a standard deviation of the Gauss function, as is the case with Equation 2, and changing a value of σ can cause an output value to change in case of performing a Log filtering process.

$$h_{gauss}(x, y) = \frac{1}{2\pi\sigma^2}\exp\left\{-\frac{(x^2+y^2)}{2\sigma^2}\right\} \quad (2)$$

$$\begin{aligned}h_{Log}(x, y) &= \nabla^2 \cdot h_{gauss}(x, y) \\ &= \left(\frac{\partial^2}{\partial x^2} + \frac{\partial^2}{\partial y^2}\right)h_{gauss} \\ &= \frac{(x^2+y^2-2\sigma^2)}{2\pi\sigma^6}\exp\left\{-\frac{(x^2+y^2)}{2\sigma^2}\right\}\end{aligned} \quad (3)$$

Also the above-described post-process for the vein pattern extraction may include, for example, a threshold process performed on image data, which has been subject to a differential filter, a binarization process, a thinning process, and the like. After having passed through the post-process, a skeleton of the vein pattern can be extracted.

The vein pattern extraction unit 241 transmits the vein pattern or the skeleton thus extracted to the fractal dimension calculation unit 251 to be described later. The vein pattern extraction unit 241 may also store the extracted vein pattern or skeleton in the storage unit 273 to be described later. It is noted that the vein pattern extraction unit 241 may store a parameter, intermediate results during the processes, and the like, which have been generated to perform each of the above-mentioned processes, in the storage unit 273.

The fractal dimension calculation unit 251 calculates fractal dimensions of a vein pattern using near-infrared light vein patterns of various magnifications transmitted from the vein pattern extraction unit 241. For example, a box-counting method, but not limited thereto, can be used as a method for calculating fractal dimensions.

The box-counting method is one that is used for calculating a fractal dimension of data acquired by an experiment and the like. The box-counting method calculates a fractal dimension $D_B$ from a number $N_\delta(F)$ of boxes required to cover a data set F, from which a fractal dimension is to be calculated, with a box having a size of δ. In the box-counting method, the fractal dimension $D_B$ can be defined in the following Equation 4.

$$D_B = -\lim_{\delta \to 0} \frac{\log N_\delta(F)}{\log \delta} \quad (4)$$

An actual fractal dimension $D_B$ can be derived by plotting a log-log graph indicating a number of boxes $N_{\delta_i}(F)$ derived for a plurality of sizes $\delta_i$ (i=1, 2, . . . , n), and deriving a gradient of the log-log graph from each of plots using a least-squares method, as shown in the following Equation 5.

$$D_B = -\frac{\log N_\delta(F)}{\log \delta} \quad (5)$$

The fractal dimension calculation unit 251 calculates fractal dimensions of near-infrared light vein patterns for respective magnifications using a method as shown in Equation 5, for example, and transmits the fractional dimensions to the pseudo-vein pattern determination unit 261 to be described later. In addition, the fractal dimension calculation unit 251 may store the calculated fractal dimensions in the storage unit 273.

The pseudo-vein pattern determination unit 261 determines presence of a pseudo-vein pattern intentionally formed on a part of the body surface H based on the fractal dimensions of the near-infrared light vein patterns for the respective magnifications transmitted from the fractal dimension calculation unit 251. In particular, the pseudo-vein pattern determination unit 261 determines the presence of the pseudo-vein pattern by comparing each of the fractal dimensions of the near-infrared light vein pattern for the respective magnifications transmitted from the fractal dimension calculation unit 251 with a predetermined threshold value. The threshold value may be, for example, a value calculated from a prior determination test using multiple estimation data or may be a value specific to a particular individual.

The pseudo-vein pattern determination unit 261 determines that no pseudo-vein patterns have been formed on the part of the body surface H when the fractal dimension transmitted from the fractal dimension calculation unit 251 is greater than the predetermined threshold value, and determines that a pseudo-vein pattern has been formed on the part of the body surface H when the fractal dimension is less than the predetermined threshold value.

The pseudo-vein pattern determination unit 261 transmits a determination result to the vein pattern registration unit 271. The pseudo-vein pattern determination unit 261 may also store the determination result in the storage unit 273. Furthermore, in storing in the storage unit, the vein pattern that has been subject to the determination and the determination result may be stored in association with each other.

Although, in the above-mentioned description, it is determined that the pseudo-vein pattern is present when the fractal dimension of the captured vein pattern is less than the predetermined threshold value, the pseudo-vein pattern may be determined to be present when the fractal dimension of the captured vein pattern is equal to or greater than a certain upper limit. This corresponds to the case where a dense pseudo-vein pattern has been formed in advance so that the pseudo-vein pattern can be imaged by capturing an image with being scaled up.

The vein pattern registration unit 271 registers a generated near-infrared light vein pattern as a template based on the determination result transmitted from the pseudo-vein pattern determination unit 261. In particular, when the determination result is transmitted from the pseudo-vein pattern determination unit 261, indicating that there is not presence of a pseudo-vein pattern, the vein pattern registration unit 271 stores the near-infrared light vein pattern transmitted from the vein pattern extraction unit 251 as a registered vein pattern in the storage unit 273. To the contrary, when the determination result is transmitted from the pseudo-vein pattern determination unit 261, indicating that there is presence of a pseudo-vein pattern, the vein pattern registration unit 271 does not register the extracted near-infrared light vein pattern and finishes a registration process. In registration of the registered vein pattern, not only the near-infrared light vein pattern is stored, but also other data for identifying an individual (for example, fingerprint data, face image data, iris data, voiceprint data, or the like) having the vein pattern may be stored in association with the near-infrared light vein pattern. Moreover, the registered vein pattern to be registered as the template may contain, for example, header information in conformity to a standard, such as a Common Biometric Exchange File Format (CBEFF) framework.

The storage unit 273 stores a registered vein pattern, which is requested to be registered from the vein pattern registration unit 271, or other data associated to the registered vein pattern. In addition to these data, imaging data generated by the imaging data generation unit 245, a vein pattern extracted by the vein pattern extraction unit 251, or the like may also be stored. Furthermore, in addition to these data, the vein pattern registration apparatus 20 can cause various parameters, intermediate results, and the like, which are needed to be stored in performing some processes, or a variety of databases and the like to be appropriately stored. This storing unit 273 can be freely read from/written to by the imaging unit 231, vein pattern extraction unit 241, fractal dimension calculation unit 251, pseudo-vein pattern determination unit 261, vein pattern registration unit 271, and the like.

The registered vein pattern disclosure unit 275 may disclose a registered vein pattern stored in the storage unit 273, for example, as required by the vein pattern authentication apparatus 30 connected to the vein pattern registration apparatus 20.

It is noted that the vein pattern registration apparatus 20 according to this embodiment may be implemented in various apparatuses, such as an information processing apparatus including a computer or a server, a mobile terminal or a personal digital assistant (PDA) including a mobile telephone or PHS, an automated teller machine (ATM), an entrance and exit control apparatus, and the like, for example.

Although in the above description, the registered vein pattern to be registered as the template has been described in a case of storing the pattern within the vein pattern registration apparatus 20, the registered vein pattern may be stored in a recording medium, such as DVD media, HD-DVD media, Blu-ray media, CompactFlash (registered trademark), memory stick, SD memory card, or the like, an IC card equipped with a non-contact IC chip, an electronic equipment, and the like.

An example of functions of vein pattern registration apparatus 20 according to this embodiment has been described above. Each of the above components may be configured using a general purpose member or circuit, or may be configured with a dedicated hardware for a function of each component. In addition, a function of each component may be achieved by only CPU or the like. Thus, a configuration used herein can be appropriately modified depending on state of the art at the time of implementing this embodiment.

(Configuration of Vein Pattern Authentication Apparatus 30)

Figure 7:
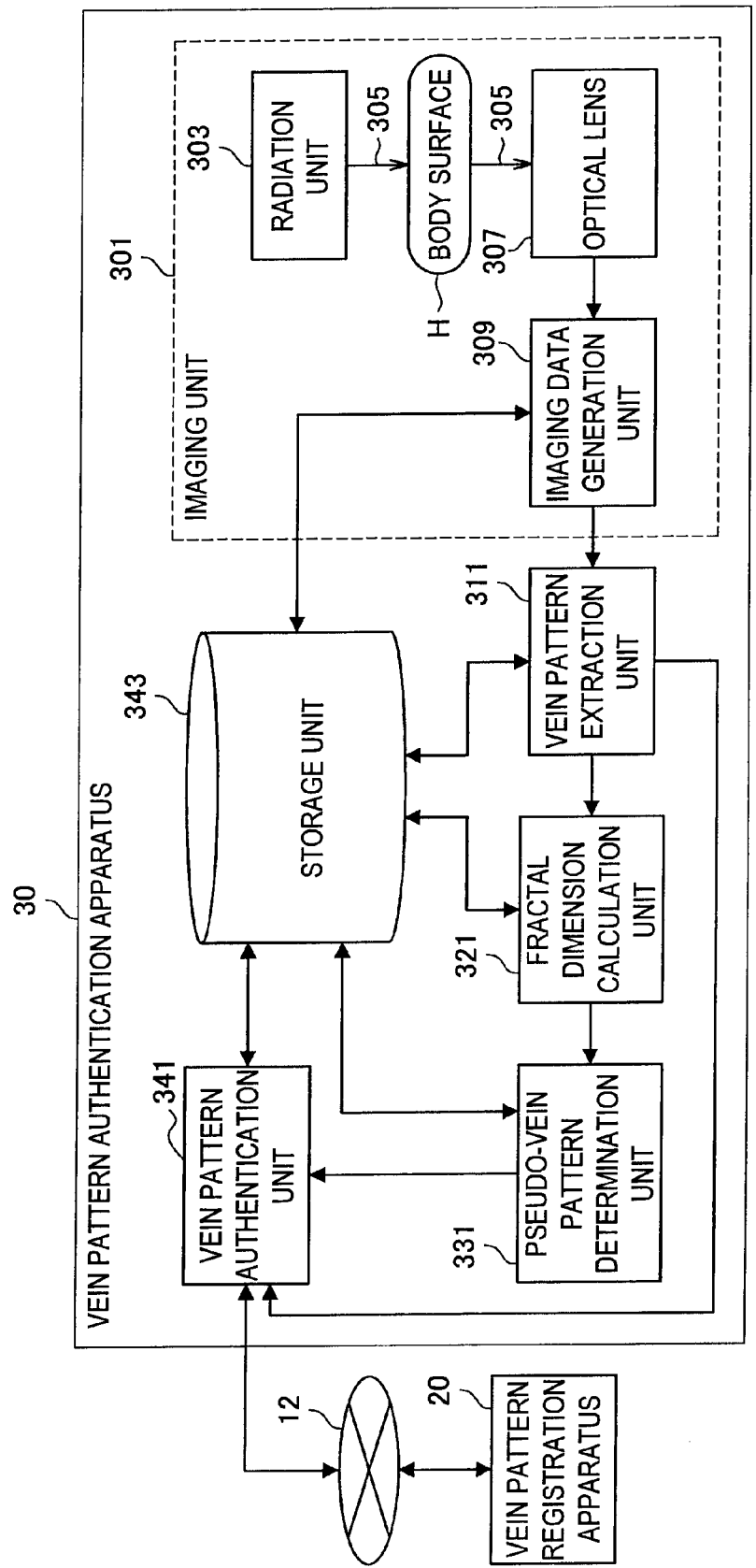
FIG. 7 is a block diagram illustrating a configuration of a vein pattern authentication apparatus according to the embodiment.

Next, referring to FIG. 7, a configuration of a vein pattern authentication apparatus 30 according to this embodiment will be described in detail. FIG. 7 is a block diagram illustrating the configuration of the vein pattern authentication apparatus 30 according to this embodiment.

As shown in FIG. 7, the vein pattern authentication apparatus 30 according to this embodiment includes, for example, an imaging unit 301, a vein pattern extraction unit 311, a fractal dimension calculation unit 321, a pseudo-vein pattern determination unit 331, a vein pattern authentication unit 341, and a storage unit 343.

The imaging unit 301 captures an image of a body surface H of an individual desiring to authenticate his/her vein pattern and generates imaging data. The imaging unit 301 includes, for example, a radiation unit 303 radiating light of a predetermined wavelength, an optical lens 307 focusing light transmitting through the body surface H, and an imaging data generation unit 309 generating imaging data based on the focused light.

The radiation unit 303 includes a light source, such as a halogen lamp and a light emitting diode, which radiates near-infrared light to the body surface H and radiates near-infrared light 305 having a wavelength of about 600 nm to about 1,300 nm.

The optical lens 307 focuses the near-infrared light 305 transmitting through the body surface H, such as a finger surface, and forms an image on the imaging data generation unit 309. The optical lens 307 according to this embodiment is capable of focusing the near-infrared light 305 by changing a magnification to a predetermined magnification. In order to focus the near-infrared light 305 to form an image at various magnifications, the optical lens 307 according to this embodiment may include multiple optical lenses having different focal lengths, respectively, or may include a multifocal lens having a variable focal length.

The imaging data generation unit 309 generates near-infrared light imaging data of various magnifications based on transmitted light of the near-infrared light 305, which has been focused by the optical lens 307. The imaging data generation unit 309 includes, for example, a CCD image sensor, a C-MOS image sensor, or the like and outputs the near-infrared light imaging data to the vein pattern extraction unit 311 to be described later. In addition, the imaging data generation unit 309 may store the generated near-infrared light imaging data in the storage unit 343 to be described later. In storing in the storage unit 343, date of capture or time of capture may be associated to the generated near-infrared light imaging data. Furthermore, the generated near-infrared light imaging data may be in the form of a Red-Green-Blue (RGB) signal or may be image data of other colors, gray scale image data, or the like.

The vein pattern extraction unit 311 includes, for example, a function of performing a pre-process for vein pattern extraction on the near-infrared light imaging data transmitted from the imaging data generation unit 309, a function of extracting a vein pattern, and a function of performing a post-process for the vein pattern extraction.

The pre-process for the vein pattern extraction includes, for example, a process for detecting a contour of a finger from near-infrared light imaging data and discriminating where the finger is located in the near-infrared light imaging data, a process for rotating the near-infrared light imaging data using the detected contour of the finger and correcting an angle of the near-infrared light imaging data (an angle of captured image), and the like.

In addition, the vein pattern extraction may be achieved by applying a differential filter to the near-infrared light imaging data, which has been subject to detecting the contour or correcting the angle. The differential filter is a filter that outputs a high value as an output value for a pixel of interest and its surrounding pixels at a portion where differences between the pixel of interest and its surrounding pixels, respectively, are large. In other words, the differential filter as used herein refers to a filter that enhances a line or an edge in an image by an operation using differences in gray level values between a pixel of interest and its surroundings.

In general, performing a filtering process on image data $u(x, y)$ with a variable, which is a lattice point $(x, y)$ on a two-dimensional plane, using a filter h(x, y) results in image data v(x, y), as shown in the following Equation 6. In the following Equation 1, * denotes convolution.

$$v(x, y) = u(x, y) * h(x, y) \quad (6)$$
$$= \sum_{m_1}\sum_{m_2} h(m_1, m_2)u(x - m_1, y - m_2)$$
$$= \sum_{m_1}\sum_{m_2} u(m_1, m_2)h(x - m_1, y - m_2)$$

In the vein pattern extraction according to this embodiment, a derivative filter, such as a first order spatial derivative filter or a second order spatial derivative filter may be used as the above-mentioned differential filter. The first order spatial derivative filter refers to a filter that, for a pixel of interest, calculates a difference in gray scale levels between the pixel of interest and its horizontally adjacent pixel or its vertically adjacent pixel, and the second order spatial derivative filter refers to a filter that extracts a portion having an increased variation in differences in gray scale values for a pixel of interest.

For example, the following Laplacian of Gaussian (Log) filter can be used as the above-mentioned second order spatial derivative filter. The Log filter (Equation 8) can be written as a second order derivative of a Gaussian filter (Equation 7), which is a smoothing filter using a Gauss function. In the following Equation 7, σ represents a standard deviation of the Gauss function, and in other words a variable representing a degree of smoothing for the Gaussian filter. Furthermore, σ in the following Equation 8 is also a parameter, which represent a standard deviation of the Gauss function, as is the case with Equation 7, and changing a value of σ can cause an output value to change in case of performing a Log filtering process.

$$h_{gauss}(x, y) = \frac{1}{2\pi\sigma^2}\exp\left\{-\frac{(x^2+y^2)}{2\sigma^2}\right\} \quad (7)$$

$$h_{Log}(x, y) = \nabla^2 \cdot h_{gauss}(x, y) \quad (8)$$
$$= \left(\frac{\partial^2}{\partial x^2} + \frac{\partial^2}{\partial y^2}\right) h_{gauss}$$
$$= \frac{(x^2 + y^2 - 2\sigma^2)}{2\pi\sigma^6}\exp\left\{-\frac{(x^2+y^2)}{2\sigma^2}\right\}$$

Also, the above-described post-process for the vein pattern extraction may include, for example, a threshold process performed on image data, which has been subject to a differential filter, a binarization process, a thinning process, and the like. After having passed through the post-process, a skeleton of the vein pattern can be extracted.

The vein pattern extraction unit 241 transmits the vein pattern or the skeleton thus extracted to the fractal dimension calculation unit 251 to be described later. The vein pattern extraction unit 241 may also store the extracted vein pattern or skeleton in the storage unit 273 to be described later. It is noted that the vein pattern extraction unit 241 may store a parameter, intermediate results during the processes, and the like, which have been generated to perform each of the above-mentioned processes, in the storage unit 273.

The fractal dimension calculation unit 321 calculates fractal dimensions of a vein pattern using near-infrared light vein patterns of various magnifications transmitted from the vein pattern extraction unit 311. For example, a box-counting method, but not limited thereto, can be used as a method for calculating fractal dimensions, and a correlation integral method may be used.

The box-counting method is one that is used for calculating a fractal dimension of data acquired by an experiment and the like. The box-counting method calculates a fractal dimension $D_B$ from a number $N_\delta(F)$ of boxes required to cover a data set F, from which a fractal dimension is to be calculated, with a box having a size of δ. In the box-counting method, the fractal dimension $D_B$ can be defined in the following Equation 9.

$$D_B = -\lim_{\delta \to 0} \frac{\log N_\delta(F)}{\log \delta} \quad (9)$$

An actual fractal dimension $D_B$ can be derived by plotting a log-log graph indicating a number of boxes $N_{\delta_i}(F)$ derived for a plurality of sizes $\delta_i$ (i=1, 2, ..., n), and deriving a gradient of the log-log graph from each of plots using a least-squares method, as shown in the following Equation 10.

$$D_B = -\frac{\log N_\delta(F)}{\log \delta} \quad (10)$$

The fractal dimension calculation unit 321 calculates fractal dimensions of near-infrared light vein patterns for respective magnifications using a method as shown in Equation 10, for example, and transmits the fractional dimensions to the pseudo-vein pattern determination unit 331 to be described later. In addition, the fractal dimension calculation unit 321 may store the calculated fractal dimensions in the storage unit 343.

The pseudo-vein pattern determination unit 331 determines presence of a pseudo-vein pattern intentionally formed on a part of the body surface H based on the fractal dimensions of the near-infrared light vein patterns for the respective magnifications transmitted from the fractal dimension calculation unit 321. In particular, the pseudo-vein pattern determination unit 331 determines the presence of the pseudo-vein pattern by comparing each of the fractal dimensions of the near-infrared light vein pattern for the respective magnifications transmitted from the fractal dimension calculation unit 321 with a predetermined threshold value. The threshold value may be, for example, a value calculated from a prior determination test using multiple estimation data or may be a value specific to a particular individual.

The pseudo-vein pattern determination unit 331 determines that no pseudo-vein patterns have been formed on the part of the body surface H when the fractal dimension transmitted from the fractal dimension calculation unit 321 is greater than the predetermined threshold value, and determines that a pseudo-vein pattern has been formed on the part of the body surface H when the fractal dimension is less than the predetermined threshold value.

The pseudo-vein pattern determination unit 331 transmits a determination result to the vein pattern authentication unit 341. The pseudo-vein pattern determination unit 331 may also store the determination result in the storage unit 343. Furthermore, in storing in the storage unit, the vein pattern that has been subject to the determination and the determination result may be stored in association with each other.

Although, in the above-mentioned description, it is determined that the pseudo-vein pattern is present when the fractal dimension of the captured vein pattern is less than the predetermined threshold value, the pseudo-vein pattern may be determined to be present when the fractal dimension of the captured vein pattern is equal to or greater than a certain upper limit. This corresponds to the case where a dense pseudo-vein pattern has been formed in advance so that the pseudo-vein pattern can be imaged by capturing an image with being scaled up.

The vein pattern authentication unit 341 performs authentication of a generated near-infrared light vein pattern based on the determination result transmitted from the pseudo-vein pattern determination unit 331. In particular, when the determination result is transmitted from the pseudo-vein pattern determination unit 331, indicating that there is not presence of a pseudo-vein pattern, for example, the vein pattern authentication unit 341 request the vein pattern registration apparatus 20 to disclose a registered vein pattern and compares the registered vein pattern acquired from the vein pattern registration apparatus 20 with the near-infrared light vein pattern transmitted from the vein pattern extraction unit 311. A process of comparing the registered vein pattern with the near-infrared light vein pattern can be achieved, for example, by calculating a correlation coefficient to be described later and performing comparison based on the calculated correlation coefficient. The vein pattern authentication unit 341 authenticates the near-infrared light vein pattern when a comparison result indicates that the registered vein pattern and the near-infrared light vein pattern are similar with each other and does not authenticate the near-infrared light vein pattern when they are not similar with each other.

The correlation coefficient is defined in the following Equation 8, is a statistical measure indicating similarity between two pieces of data: $x=\{x_i\}$ and $y=\{y_i\}$, and has a real value from $-1$ to $1$. When the correlation coefficient has a value close to 1, it indicates that the two pieces of the data are similar with each other, and when the correlation coefficient has a value close to 0, it indicates that the two pieces of the data are not similar with each other. In addition, when the correlation coefficient has a value close to $-1$, it indicates a case where the two pieces of the data have inverted signs, respectively.

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad (11)$$

$\bar{x}$: Average of Data x $\bar{y}$: Average of Data y

To the contrary, when the determination result is transmitted from the pseudo-vein pattern determination unit 331, indicating that there is presence of a pseudo-vein pattern, the vein pattern authentication unit 341 does not perform and finishes an authentication process of the extracted near-infrared light vein pattern.

The storage unit 343 is capable of storing imaging data generated by the imaging data generation unit 309, the vein pattern extracted by the vein pattern extraction unit 311, or the like. Furthermore, in addition to these data, the vein pattern authentication apparatus 30 can cause various parameters, intermediate results, and the like, which are needed to be stored in performing some processes, or a variety of databases and the like to be appropriately stored. This storing unit 343 can be freely read from/written to by the imaging unit 301, vein pattern extraction unit 311, fractal dimension calculation unit 321, pseudo-vein pattern determination unit 331, vein pattern authentication unit 341, and the like.

The vein pattern authentication apparatus 30 according to this embodiment may be implemented in various apparatuses, such as an information processing apparatus including a computer or a server, a mobile terminal or a personal digital assistant (PDA) including a mobile telephone or PHS, an automated teller machine (ATM), an entrance and exit control apparatus, and the like, for example.

Although in the above description, the registered vein pattern is supposed to be acquired from the vein pattern registration apparatus 20, the authentication may be performed based on the registered vein pattern, which has been stored in a recording medium, such as DVD media, HD-DVD media, Blu-ray media, CompactFlash (registered trademark), memory stick, SD memory card, or the like, an IC card equipped with a non-contact IC chip, an electronic equipment, and the like. Furthermore, the registered vein pattern may be stored in the vein pattern authentication apparatus 30.

An example of functions of vein pattern authentication apparatus 30 according to this embodiment has been described above. Each of above components may be configured using a general purpose member or circuit, or may be configured with a dedicated hardware for a function of each component. In addition, a function of each component may be achieved by only CPU or the like. Thus, a configuration used herein can be appropriately modified depending on state of the art at the time of implementing this embodiment.

(Registration Method of Vein Pattern)

Figure 8:
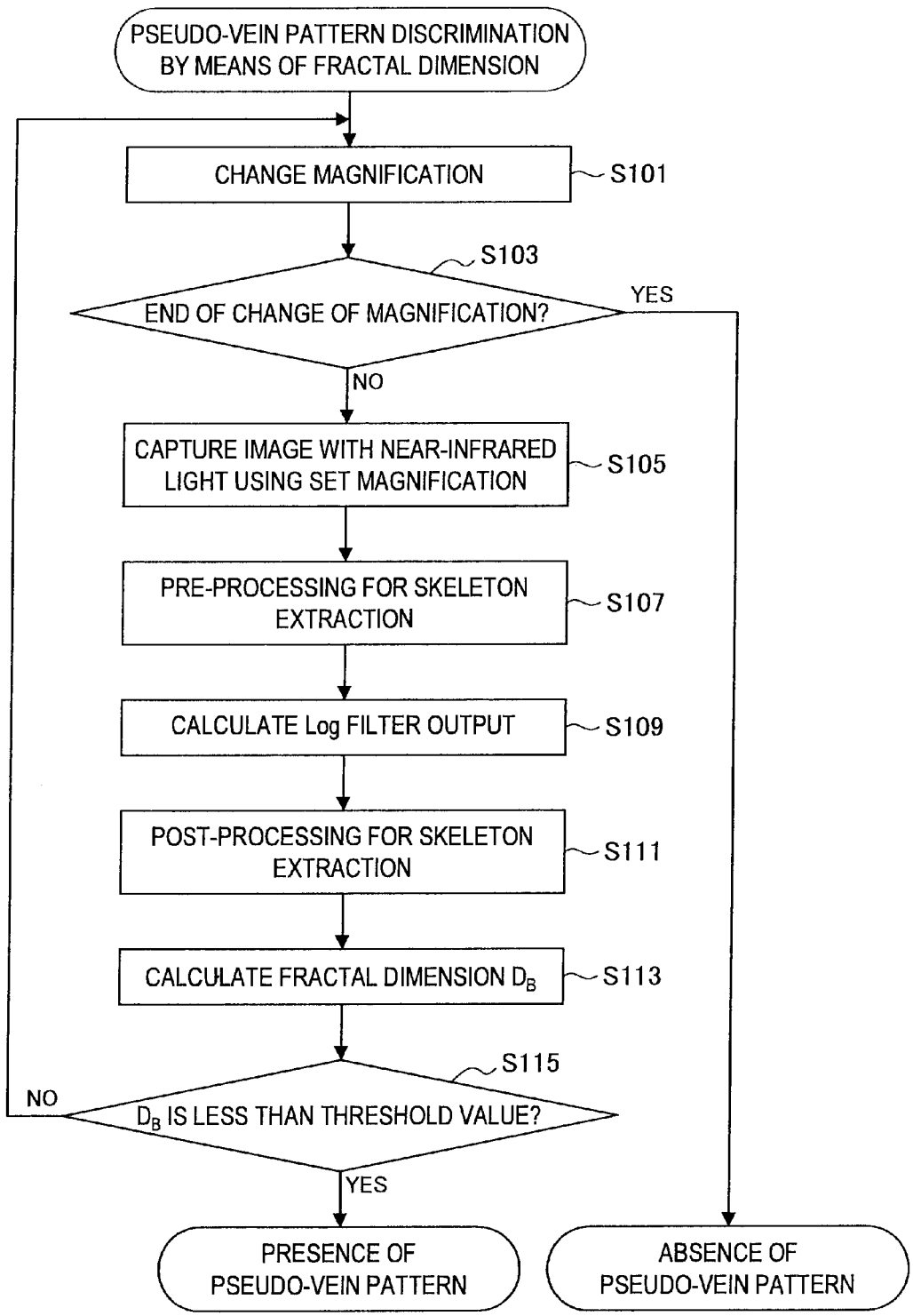
FIG. 8 is a flowchart illustrating a pseudo-vein pattern discrimination method by means of a fractal dimension according to the embodiment.

Next, referring to FIG. 8, a method for registering a vein pattern according to this embodiment will be described in detail. FIG. 8 is a flowchart illustrating a method for discriminating pseudo-vein patterns according to this embodiment.

It is known that a blood vessel in a body has a self-similarity. Therefore, the method for registering a vein pattern according to this embodiment is characterized in that fractal dimensions of vein patterns captured by changing a magnification are calculated and presence of a pseudo-vein pattern is determined based on the calculated fractal dimensions.

Although, in the following description, an object to be imaged is captured with three different magnifications including a magnification of 1 (capture with full-scale), a magnification of 1.5 (capture with magnification of 1.5), and a magnification of 2 (capture with magnification of 2), a selection of the magnification in the method for registering a vein pattern according to this embodiment is not limited to the above-mentioned examples.

Firstly, an imaging unit 231 in a vein pattern registration apparatus 20 sets a magnification of an optical lens 237 in the imaging unit 231 to 1 and controls the optical lens 237 such that an object to be imaged is captured without scaling up (step S101). The imaging unit 231 then captures an image of a part of a body surface (for example, a finger surface) with near-infrared light without scaling up, and an imaging data generation unit 239 in the imaging unit 231 generates near-infrared light imaging data (step S105). The imaging data generation unit 239 stores the generated near-infrared light imaging data in a storage unit 273, for example, in association with date of capture or time of capture, and transmits the generated near-infrared light imaging data to a vein pattern extraction unit 241.

The vein pattern extraction unit 241, to which the near-infrared light imaging data transmitted, performs a pre-process for skeleton extraction of a vein pattern on the near-infrared light imaging data, in which the pre-process includes a process for detecting a contour of a finger and discriminating a position of the finger, or a process for rotating the near-infrared light imaging data and correcting an angle of the near-infrared light imaging data (step S107).

Once the pre-process for the skeleton extraction has finished, the vein pattern extraction unit 241 then calculates a Log filter output by applying a Log filter process, which is a kind of differential filters, to the near-infrared light imaging data, which has been subject to the pre-process (step S109), to generate a near-infrared light vein pattern. Next, the vein pattern extraction unit 241 applies a post-process, such as a threshold process, a binarization process, and a thinning process, to the generated near-infrared light vein pattern (step S111), stores the near-infrared light vein pattern that has been subject to the post-process in a storage unit 273 as well as transmits the near-infrared light vein pattern to the fractal dimension calculation unit 251.

The fractal dimension calculation unit 251 calculates a fractal dimension $D_B$ by a box-counting method using the near-infrared light pattern, which has been transmitted from the vein pattern extraction unit 241, with the magnification of 1 (step S113). In particular, while changing a size δ of a box, a number of boxes covering the near-infrared vein pattern is counted, and a log-log graph is plotted by taking the number of the boxes as an ordinate axis and the size of the box as an abscissa axis. A least-squares method is applied to each of plotted points to calculate a gradient and the calculated gradient is assigned to a fractal dimension $D_B$ of the near-infrared light vein pattern captured with the magnification of 1. The fractal dimension calculation unit 251 transfers the calculated fractal dimension $D_B$ to a pseudo-vein pattern determination unit 261 as well as stores the calculated fractal dimension $D_B$ in the storage unit 273.

The pseudo-vein pattern determination unit 261 determines presence of a pseudo-vein pattern by comparing the fractal dimension transmitted from the fractal dimension calculation unit 251 with a threshold value of the fractal dimension (step S115). In particular, the pseudo-vein pattern determination unit 261 compares a magnitude of the fractal dimension $D_B$ transmitted from the fractal dimension calculation unit 251 with that of the predetermined threshold value of the fractal dimension and determines that the pseudo-vein pattern is present and finishes a registration process for a registered pattern when the transmitted fractal dimension $D_B$ is less than the threshold value. Otherwise, when the transmitted fractal dimension $D_B$ is equal to or greater than the threshold value, the imaging unit 231 is informed of this accordingly.

Secondly, the imaging unit 231 sets the magnification of the optical lens 237 in the imaging unit 231 to 1.5 and controls the optical lens 237 such that a finger surface, which is the object to be imaged, is captured with a scale of 1.5 (step S101). Then, in the same manner as described above, the fractal dimension $D_B$ is calculated and the calculated fractal dimension $D_B$ is compared with a predetermined threshold value. Also, in case of the magnification of 1.5, when the transmitted fractal dimension $D_B$ is equal to or greater than the threshold value, the pseudo-vein pattern determination unit 261 informs the imaging unit 231 of this accordingly.

Subsequently, the imaging unit 231 sets the magnification of the optical lens 237 in the imaging unit 231 to 2, controls the optical lens 237 such that a finger surface, which is the object to be imaged, is captured with a scale of 2 (step S101), and performs a comparison of the fractal dimension $D_B$ in the same manner as described above.

In either cases where the magnification is 1, 1.5, or 2, when the calculated fractal dimension $D_B$ is equal to or greater than a predetermined threshold value, a change in the magnification is supposed to be finished (step S103), and the pseudo-vein pattern determination unit 261 informs the vein pattern registration unit 271 of the fact that the pseudo-vein pattern is not present.

When the vein pattern registration unit 271 is informed of a signal indicating that there are no pseudo-vein patterns present from the pseudo-vein pattern determination unit 261, the vein pattern registration unit 271 stores the near-infrared light vein pattern subject to the post-process and transmitted from the vein pattern extraction unit 241 as a registered vein pattern in a database (not shown) contained in the storage unit 273. In addition, the registered vein pattern may be associated with ID or other biometrics data of an individual, or the like.

Furthermore, when the vein pattern registration unit 271 is informed of a signal indicating that there is a pseudo-vein pattern present from the pseudo-vein pattern determination unit 261, the vein pattern registration unit 271 does not perform a registration process of the vein pattern and finishes a series of processes.

As described above, in the method for registering a vein pattern according to this embodiment, it is possible to determine presence of a pseudo-vein pattern intentionally formed on a part of a body surface by focusing attention on a fractal dimension of a captured near-infrared light vein pattern. Since a method for registering a vein pattern according to this embodiment can determine presence of a pseudo-vein pattern before registering the vein pattern, possibility of storing unnecessary data in a database and the like, in which registered vein patterns are contained, is avoided, and it becomes easy to manage the registered vain patterns.

(Authentication Method of Vein Pattern)

Next, again referring to FIG. 8, a method for authenticating a vein pattern according to this embodiment will be described in detail.

It is known that a blood vessel in a body has a self-similarity. Therefore, the method for authenticating a vein pattern according to this embodiment is characterized in that fractal dimensions of vein patterns captured by changing a magnification are calculated and presence of a pseudo-vein pattern is determined based on the calculated fractal dimensions.

Although, in the following description, an object to be imaged is captured with three different magnifications including a magnification of 1 (capture with full-scale), a magnification of 1.5 (capture with magnification of 1.5), and a magnification of 2 (capture with magnification of 2), a selection of the magnification in the method for authenticating a vein pattern according to this embodiment is not limited to the above-mentioned examples.

Firstly, an imaging unit 301 in a vein pattern authentication apparatus 30 sets a magnification of an optical lens 307 in the imaging unit 301 to 1 and controls the optical lens 307 such that an object to be imaged is captured without scaling up (step S101). The imaging unit 301 then captures an image of a part of a body surface (for example, a finger surface) with near-infrared light without scaling up, and an imaging data generation unit 309 in the imaging unit 301 generates near-infrared light imaging data (step S105). The imaging data generation unit 309 stores the generated near-infrared light imaging data in a storage unit 343, for example, in association with date of capture or time of capture, and transmits the generated near-infrared light imaging data to a vein pattern extraction unit 311.

The vein pattern extraction unit 311, to which the near-infrared light imaging data transmitted, performs a pre-process for skeleton extraction of a vein pattern on the near-infrared light imaging data, in which the pre-process includes a process for detecting a contour of a finger and discriminating a position of the finger, or a process for rotating the near-infrared light imaging data and correcting an angle of the near-infrared light imaging data (step S107).

Once the pre-process for the skeleton extraction has finished, the vein pattern extraction unit 311 then calculates a Log filter output by applying a Log filter process, which is a kind of differential filters, to the near-infrared light imaging data, which has been subject to the pre-process (step S109), to generate a near-infrared light vein pattern. Next, the vein pattern extraction unit 311 applies a post-process, such as a threshold process, a binarization process, and a thinning process, to the generated near-infrared light vein pattern (step S111), stores the near-infrared light vein pattern that has been subject to the post-process in a storage unit 343 as well as transmits the near-infrared light vein pattern to the fractal dimension calculation unit 321.

The fractal dimension calculation unit 321 calculates a fractal dimension $D_B$ by a box-counting method using the near-infrared light pattern, which has been transmitted from the vein pattern extraction unit 311, with the magnification of 1 (step S113). In particular, while changing a size δ of a box, a number of boxes covering the near-infrared vein pattern is counted, and a log-log graph is plotted by taking the number of the boxes as an ordinate axis and the size of the box as an abscissa axis. A least-squares method is applied to each of plotted points to calculate a gradient and the calculated gradient is assigned to a fractal dimension $D_B$ of the near-infrared light vein pattern captured with the magnification of 1. The fractal dimension calculation unit 321 transfers the calculated fractal dimension $D_B$ to a pseudo-vein pattern determination unit 331 as well as stores the calculated fractal dimension $D_B$ in the storage unit 343.

The pseudo-vein pattern determination unit 331 determines presence of a pseudo-vein pattern by comparing the fractal dimension transmitted from the fractal dimension calculation unit 321 with a threshold value of the fractal dimension (step S115). In particular, the pseudo-vein pattern determination unit 331 compares a magnitude of the fractal dimension $D_B$ transmitted from the fractal dimension calculation unit 321 with that of the predetermined threshold value of the fractal dimension and determines that the pseudo-vein pattern is present and finishes a registration process for a registered pattern when the transmitted fractal dimension $D_B$ is less than the threshold value. Otherwise, when the transmitted fractal dimension $D_B$ is equal to or greater than the threshold value, the imaging unit 301 is informed of this accordingly.

Secondly, the imaging unit 301 sets the magnification of the optical lens 307 in the imaging unit 301 to 1.5 and controls the optical lens 307 such that a finger surface, which is the object to be imaged, is captured with a scale of 1.5 (step S101). Then, in the same manner as described above, the fractal dimension $D_B$ is calculated and the calculated fractal dimension $D_B$ is compared with a predetermined threshold value. Also, in case of the magnification of 1.5, when the transmitted fractal dimension $D_B$ is equal to or greater than the threshold value, the pseudo-vein pattern determination unit 311 informs the imaging unit 231 of this accordingly.

Subsequently, the imaging unit 301 sets the magnification of the optical lens 307 in the imaging unit 301 to 2, controls the optical lens 307 such that a finger surface, which is the object to be imaged, is captured with a scale of 2 (step S101), and performs a comparison of the fractal dimension $D_B$ in the same manner as described above.

In either cases where the magnification is 1, 1.5, or 2, when the calculated fractal dimension $D_B$ is equal to or greater than a predetermined threshold value, a change in the magnification is supposed to be finished (step S103), and the pseudo-vein pattern determination unit 331 informs the vein pattern authentication unit 341 of the fact that the pseudo-vein pattern is not present.

When the vein pattern authentication unit 341 is informed of a signal indicating that there are no pseudo-vein patterns present from the pseudo-vein pattern determination unit 331, the vein pattern authentication unit 341 requests the vein pattern registration apparatus 20 to disclose a registered vein pattern. Once the registered vein pattern has been disclosed by a registered vein pattern disclosure unit 275 in the vein pattern registration apparatus 20, the vein pattern authentication unit 341 acquires and compares the disclosed registered vein pattern with the near-infrared light vein pattern, which has been subject to the post-process, transmitted from the vein pattern extraction unit 311. Comparison of the registered vein pattern with the near-infrared light vein pattern is performed, for example, using a method capable of quantitatively calculating similarity, such as above-mentioned correlation coefficient, between image data. The vein pattern authentication unit 341 authenticates the generated near-infrared light vein pattern when the registered vein pattern and the near-infrared light vein pattern are similar with each other, but the vein pattern authentication unit 341 does not authenticate the near-infrared light vein pattern when they are not similar with each other.

Furthermore, when the vein pattern authentication unit 341 is informed of a signal indicating that there is a pseudo-vein pattern present from the pseudo-vein pattern determination unit 331, the vein pattern authentication unit 341 does not perform an authentication process of the vein pattern and finishes a series of processes.

As described above, in the method for authenticating a vein pattern according to this embodiment, it is possible to determine presence of a pseudo-vein pattern intentionally formed on a part of a body surface by focusing attention on a fractal dimension of a captured near-infrared light vein pattern. Since a method for authenticating a vein pattern according to this embodiment can determine presence of a pseudo-vein pattern before authenticating the vein pattern, it can previously prevent malicious users from impersonating others by repeating try and error to optimize a pseudo-vein pattern.

(Vein Data Configuration)

Furthermore, according to an embodiment of the present invention, a vein data configuration is provided in which the vein data configuration includes a vein data storage area containing data, which correspond to a vein pattern of an individual and are to be verified with image data acquired by capturing an image of a part of a body surface of a living body with near-infrared light, and fractal dimension storage area containing a fractal dimension of the vein pattern of the individual.

The vein data storage area is an area containing, for example, a vein pattern that has been registered as a registered vein pattern by the vein pattern registration apparatus 20. The data contained in this vein data storage area are used, for example, by the vein pattern authentication apparatus 30 in authenticating a near-infrared light vein pattern captured.

The fractal dimension storage area is an area in which the fractal dimension of the vein pattern of the individual is contained, and the fractal dimension contained in this fractal dimension storage area is used, for example, by the vein pattern registration apparatus 20 or the vein pattern authentication apparatus 30 to determine presence of a pseudo-vein pattern formed on a body surface.

The above-mentioned vein data configuration further includes a parameter storage area containing a parameter, which changes an output property of a differential filter outputting a high output for an pixel that differs largely from its surrounding pixels, for each pixel constituting the image data acquired by capturing the image with the near-infrared light.

The parameter contained in the parameter storage area is a parameter for a differential filter used, for example, by the vein pattern registration apparatus 20 or the vein pattern authentication apparatus 30 in extracting a vein pattern from imaging data captured with near-infrared light or visible light, and the parameter significantly changes an output value of the differential filter, for example, when the image data acquired by capturing the image with the near-infrared light have a difference greater than that between a value indicating a vein portion and a value indicating a non-vein portion.

The above-mentioned parameter is separately contained for each type of differential filters and makes a pseudo-vein pattern formed on the body surface have a value such that the pseudo-vein pattern can be detected by the differential filter. For example, when a Log filter is used as the differential filter, a value, by which the Log filter can detect the pseudo-vein pattern, is contained in the parameter storage area. In this case, the value of the parameter to be contained is equal to or greater than 2.0.

The above-mentioned vein data configuration can be applied to, for example, a non-contact IC chip, or an IC card, such as a Subscriber Identity Module (SIM) card, used in a mobile telephone and the like. In addition, this vein data configuration can be applied to a recording medium, such as a DVD medium, a HD-DVD medium, a Blu-ray medium, CompactFlash (registered trademark), a memory stick, or a SD memory card.

It should be understood by those skilled in the art that various modifications, combinations, sub-combinations and alterations may occur depending on design requirements and other factors insofar as they are within the scope of the appended claims or the equivalents thereof.

For example, although in the above-mentioned embodiments, it has been described that a vein pattern registration apparatus 20 and a vein pattern authentication apparatus 30 are separately provided, respectively, a vein pattern management apparatus including functions of both a vein pattern registration apparatus 20 and a vein pattern authentication apparatus 30 may be provided.

Furthermore, although in the above-mentioned embodiments, it has been described that a transmissive imaging unit is provided each of a vein pattern registration apparatus 20 and a vein pattern authentication apparatus 30, a reflective imaging unit may be provided depending on a portion of a body surface to be captured.

The invention claimed is:

1. A vein pattern management system for registering and authenticating a vein pattern acquired by radiating light to a portion of a living body, comprising:

an imaging unit for capturing an image of a body surface of the portion of the living body with near-infrared light while changing a magnification, and generating multiple pieces of near-infrared light imaging data having different magnifications;

a vein pattern extraction unit for extracting multiple vein patterns corresponding to each of the multiple pieces of the near-infrared light imaging data from each of the multiple pieces of the near-infrared light imaging data;

a fractal dimension calculation unit for calculating a fractal dimension corresponding to each of the vein patterns for the extracted multiple vein patterns;

a pseudo-vein pattern determination unit for determining presence of a pseudo-vein pattern intentionally formed on a part of the captured body surface based on the calculated fractal dimension;

a vein pattern registration unit for registering the near-infrared light vein pattern based on a determination result from the determination unit to generate a registered vein pattern; and a vein pattern authentication unit for comparing a newly generated near-infrared light vein pattern with the registered vein pattern based on the determination result from the pseudo-vein pattern determination unit and authenticating the newly generated near-infrared vein pattern.

2. The vein pattern management system according to claim 1, wherein
the pseudo-vein pattern determination unit determines that the pseudo-vein pattern is present when the calculated fractal dimension is less than a predetermined threshold value of a fractal dimension, and determines that the pseudo-vein pattern is not present when the calculated fractal dimension is greater than the predetermined threshold value of the fractal dimension.

3. The vein pattern management system according to claim 1, wherein
the fractal dimension calculation unit calculates the fractal dimension using a box-counting method for a plurality of pixels constituting the vein pattern.

4. The vein pattern management system according to claim 1, wherein
the vein pattern extraction unit extracts the near-infrared light vein pattern using a differential filter that outputs a large value for a pixel having a large difference between the pixel and its surrounding pixel for a plurality of pixels constituting the near-infrared light imaging data.

5. The vein pattern management system according to claim 4, wherein
the differential filter is a derivative filter.

6. The vein pattern management system according to claim 5, wherein
the differential filter is a Laplacian of Gaussian (Log) filter.

* * * * *